(12) United States Patent
Alcantar et al.

(10) Patent No.: US 9,522,114 B1
(45) Date of Patent: Dec. 20, 2016

(54) ENHANCED TARGETED DRUG DELIVERY SYSTEM VIA CHITOSAN HYDROGEL AND CHLOROTOXIN

(71) Applicants: Norma A. Alcantar, Tampa, FL (US); Rana Falahat, Tampa, FL (US); Marzenna Wiranowska, Lutz, FL (US); Ryan G. Toomey, Tampa, FL (US)

(72) Inventors: Norma A. Alcantar, Tampa, FL (US); Rana Falahat, Tampa, FL (US); Marzenna Wiranowska, Lutz, FL (US); Ryan G. Toomey, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/671,439

(22) Filed: Mar. 27, 2015

Related U.S. Application Data

(60) Provisional application No. 61/971,328, filed on Mar. 27, 2014.

(51) Int. Cl.
| | | |
|---|---|---|
| A61K 38/00 | (2006.01) | |
| A61K 9/127 | (2006.01) | |
| A61K 31/337 | (2006.01) | |
| A61K 47/36 | (2006.01) | |
| A61K 38/17 | (2006.01) | |
| A61K 9/06 | (2006.01) | |
| A61K 47/24 | (2006.01) | |

(52) U.S. Cl.
CPC ............ *A61K 9/127* (2013.01); *A61K 9/06* (2013.01); *A61K 9/1277* (2013.01); *A61K 31/337* (2013.01); *A61K 38/1767* (2013.01); *A61K 47/24* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 4,830,857 A | 5/1989 | Handjani et al. | |
| 4,873,088 A | 10/1989 | Mayhew et al. | |
| 4,891,208 A | 1/1990 | Janoff et al. | |
| 4,912,032 A | 3/1990 | Hoffman et al. | |
| 5,262,055 A | 11/1993 | Bae et al. | |
| 5,575,815 A | 11/1996 | Slepian et al. | |
| 5,741,515 A | 4/1998 | Ciceri et al. | |
| 6,344,488 B1 | 2/2002 | Chenite et al. | |
| 6,403,056 B1 | 6/2002 | Unger | |
| 6,428,811 B1 | 8/2002 | West et al. | |
| 6,486,213 B1 | 11/2002 | Chen et al. | |
| 2002/0143385 A1 | 10/2002 | Yang | |
| 2002/0146750 A1* | 10/2002 | Hoogenboom | A61K 47/48538 435/7.23 |
| 2004/0047892 A1 | 3/2004 | Desrosiers et al. | |
| 2004/0225077 A1 | 11/2004 | Gravett et al. | |
| 2004/0248294 A1 | 12/2004 | Chopart et al. | |
| 2006/0166892 A1* | 7/2006 | Alvarez | A61K 31/00 514/15.2 |
| 2010/0068264 A1* | 3/2010 | Alcantar | A61K 47/36 424/450 |

OTHER PUBLICATIONS

Non-final office action issued by the USPTO on Apr. 28, 2009 for corresponding U.S. Appl. No. 11/737,271.
Final office action issued by the USPTO on Nov. 5, 2009 for corresponding U.S. Appl. No. 11/737,271.
Non-final office action issued by the USPTO on May 3, 2010 for corresponding U.S. Appl. No. 11/737,271.
Final office action issued by the USPTO on Dec. 15, 2010 for corresponding U.S. Appl. No. 11/737,271.
Non-final office action issued by the USPTO on Aug. 4, 2011 for corresponding U.S. Appl. No. 11/737,271.
Non-final office action issued by the USPTO on Oct. 28, 2011 for corresponding U.S. Appl. No. 12/622,693.
Final office action issued by the USPTO on May 17, 2012 for corresponding U.S. Appl. No. 12/622,693.
Non-final office action issued by the USPTO on Jul. 17, 2014 for corresponding U.S. Appl. No. 12/622,693.
Final office action issued by the USPTO on Apr. 16, 2015 for corresponding U.S. Appl. No. 12/622,693.
Triton X-100. Roche Diagnostics GmbH. Roche Applied Science, Manhaim, Germany. Cat. No. 11 332 481 001. www.roche-applied-science.com. Version Sep. 2005.
Time release technology. Wikipedia. http://en.wikipedia.org/wiki/Time_release_techonolgy. Accessed on Apr. 13, 2011.
Sn-glycerol-3-phosphate—Compound summary (CID 439162). PubChem Public Chemical Database. http://pubchem.ncbi.nlm.nih.gov/summary/summary.cgi?cid=439162&loc=ec_rcs. Accessed on Apr. 15, 2011.
Beta-glycerophosphoric acid—Compound summary (CID 2526). PubChem Public Chemical Database. http://pubchem.ncbi.nlm.nih.gov/summary/summary.cgi?cid=2526&loc=ec_rcs. Accessed on Apr. 15, 2011.
Alpha-glycerophosphoric acid—Compound summary (CID 754). PubChem Public Chemical Database. http://pubchem.ncbi.nlm.nih.gov/summary/summary.cgi?cid=754&loc=ec_rcs. Accessed on Apr. 15, 2011.

(Continued)

*Primary Examiner* — Jeanette Lieb
(74) *Attorney, Agent, or Firm* — Robert J. Varkonyi; Smith & Hopen, P.A.

(57) ABSTRACT

Specific drug delivery to tumor cells without affecting normal cells is a major challenge in cancer treatment. The present invention incorporates embedding nonionic surfactant vesicles (niosomes) containing an anti-cancer therapeutic agent with chlorotoxin into a thermosensitive chitosan hydrogel network. Chitosan has mucoadhesive property which can be used in the targeting of the tumor cells with the mucin over expression. Chlorotoxin is a 36 amino acid peptide obtained from *Leiurus quinquestriatus* scorpion venom which binds preferentially to tumor cells of neuroectodermal origin but not to normal cells. The incorporation of chlorotoxin along with niosomes in the chitosan hydrogel is used as the second targeting strategy to further improve the specific delivery of drugs to tumor cells such as glioma.

21 Claims, 29 Drawing Sheets

(56) References Cited

OTHER PUBLICATIONS

Cho, Y.I. and J.P. Hartnett. The Falling Ball Viscometer—A New Instrument for Viscoelastic Fluids. Letters in Heat and Mass Transfer. vol. 6 pp. 335-342, 1979.

Hood, Elizabeth et al. Ultrasound Enhancement of Drug Release Across Non Ionic Surfactant Vesicle Membranes. Proceedings of the 26th Annual International Conference of the IEEE EMBS. San Fransisco, CA, USA. Sep. 1-5, 2004, pp. 3527-3530.

Behjat, T. et al. Effect of PEG on the biodegradability studies of Kenaf cellulose—polyethylene composites. International Food Research Journal 16: 243-247 (2009).

Dwyer, Daryl F. and James M. Tiedje. Degradation of Ethylene Glycol and Polyethylene Glycols by Methanogenic Consortia. Applied and Environmental Microbiology, Jul. 1983, vol. 46, No. 1, p. 185-190.

Dang, Wenbin et al. Effects of GLIADEL wafer initial molecular weight on the erosion of wafer and release of BCNU. Journal of Controlled Release, 42 (1996), p. 83-92.

McGovern, P.C. et al. Risk Factors for Postcraniotomy Surgical Site Infection after 1,3-Bis (2-Chloroethyl)-1-Nitrosourea (Gliadel) Wafer Placement. Gliadel Wafer Surgery Infections, CID 2003:36 (Mar. 2015), p. 759-765.

Israelachvilli. Aggregation of Amphiphilic Molecules into Micelles, Bilayers, Vesicles and Biological Membranes. Intermolecular and Surface Forces, Table 16.1 and Chapter 17, p. 366-394.

Guo, J. et al. Chitosan-coated liposomes: characterization and interaction with leuprolide. International Journal of Pharmaceutics 260 (2003) 167-173.

Pozzi, Daniela et al. Effect of Cholesterol on the Formation and Hydration Behavior of Solid Supported Niosomal Membranes. Langmuir 2010, 26 (4), 2268-2273.

Henriksen, Ingrid et al. Interactions between liposomes and chitosan II: effect of selected parameters on aggregation and leakage. International Journal of Pharmaceutics 146 (1997) 193-204.

De Gier, J. et al. Lipid Composition and Permeability of Liposomes. Biochim Biophys. Acta, 150 (1968) 666-675.

Sahin, Nefise Ozlen. Niosomes as Nanocarrier Systems. M.R. Mozafari (ed.), Nanomaterials and Nanosystems for Biomedical Applications. Chapter 4, p. 67-81.

Plumb, J.A. et al. Optimization of a Chemosensitivity Assay Based on Reduction of the Tetrazolium Dye. Anticancer Research. vol. 7 (1987). No. 5. pp. 902.

Tiukinhoy, Susan D. et al. Novel Echogenic Drug-Immunoliposomes for Drug Delivery. Investigative Radiology. vol. 39, No. 2, Feb. 2004. p. 104-110.

Villanueva, F.S. et al. Microbubbles Targeted to Intercellular Adhesion Molecule-1 Bind to Activated Coronary Artery Endothelial Cells. Circulation. Journal of the American Heart Association, Vol. 98. pp. 1-5.

Greenlee R.T. et al. Cancer Statistics, 2001. CA Cancer J. Clin 2001; 51; 15-36.

Jemal, A. et al. Cancer Statistics, 2002. CA Cancer J. Clin 2002; 52; 23-47.

Nounou M.M. et al. In vitro release of hydrophilic and hydrophobic drugs from liposomal dispersions and gels. Acta Pharm. 56 (2006)—311-324.

Schwartz, Peter E. and Kenneth J.W. Taylor. Is Early Detection of Ovarian Cancer Possible? Annals of medicine, 1995. 27; 519-528.

Blok, M.C. et al. The Effect of Cholesterol Incorporation on the Temperature Dependence of Water Permeation through Liposomal Membranes Prepared from Phosphatidylcholines. Biochimica et Biophysica Acta, 464 (1977) 509-518.

Armstrong, Deborah K. et al. Intraperitoneal Cisplatin and Paclitaxel in Ovarian Cancer. N. Engl J. Med., Jan. 5, 2006. 354; 1; 34-43.

Markman, Maurie et al. Combination Intraperitoneal Chemotherapy with Cisplatin, Cytarabine, and Doxorubicin for Refractory Ovarian Carcinoma and Other Malignancies Principally Confined to the Peritoneal Cavity. Journal of Clinical Oncology, vol. 2, No. 12 Dec. 1984. p. 1321-1326.

Hamilton, Chad A. and Jonathan S. Berek. Intraperitoneal chemotherapy for ovarian cancer. Current Opinion in Oncology. vol. 18. pp. 507-515.

Gore, Martin. Intraperitoneal Chemotherapy in Ovarian Cancer Remains Experimental. Journal of Clinical Oncology. vol. 24, No. 28. Oct. 1, 2006; pp. 4528-4530.

Bertozzi, Cara A. et al. Multiple Initial Culture Conditions Enhance the Establishment of Cell Lines from Primary Ovarian Cancer Specimens. In Vitro Cell. Dev. Biol-Animal 42:58-62, Mar. and Apr. 2006.

Fernando, Augusta. Effect of culture conditions on the chemosensitivity of ovarian cancer cell lines. Anti-Cancer Drugs 2006, vol. 17, No. 8, pp. 913-919.

Bengt Fadeel. Clear and present danger? Engineered nanoparticles and the immune system, Swiss Med Wkly. 2012, 142:w13609.

Kan, Pei et al. A Liposomal Formulation Able to Incorporate a High Content of Paclitaxel and Exert Promising Anticancer Effect. Journal of Drug Delivery, vol. 2011, Article ID 629234, pp. 1-9.

Mohammed, A.R. et al. Liposome formulation of poorly water soluble drugs: optimisation of drug loading and ESEM analysis of stability. International Journal of Pharmaceutics 285 (2004)—23-34.

Dearborn, Kristina Ok-Hee. The Characterization of Non-Ionic Surfactant Vesicles: A Release Rate Study for Drug Delivery, 2006, University of South Florida.

Darwish, Inas A. and Ijeoma F. Uchegbu. The evaluation of crown ether based niosomes as cation containing and cation sensitive drug delivery systems. International Journal of Pharmaceutics 159 (1997) 207-213.

Echegoyen, Lourdes E. et al. Aggregation of Steroidal Lariat Ethers: The First Example of Nonionic Liposomes (Niosomes) formed from Neurtral Crown Ether Compounds. J. Chem. Soc., Chem. Commun., 1988. pp. 836-837.

Monserrat, Keith et al. Light-Induced Charge Injection in Functional Crown Ether Vesicles. J. Am. Chem. Soc. 1980, 102,5527-5529.

Uchegbu, Ijeoma F. and Ruth Duncan. Niosomes containing N-(2-hydroxypropyl)methacrylamide copolymer-doxorubicin (PK1): effect of method of preparation and choice of surfactant on niosome characteristics and a preliminary study of body distribution. International Journal of Pharmaceutics 155 (1997) 7-17.

Gillies, R.J. et al. 3P-MRS measurements of extracellular pH of tumors using 3-aminopropylphosphonate. Am. J. Phys. Cell. Physiol., 1994. vol. 267, pp. C195-C203.

Makino, Kimiko et al. Temperature- and ionic strength-induced conformational changes in the lipid head group region of liposomes as suggested by zeta potential data. Biophysical Chemistry 41 (1991) 175-183.

Chenite, et al., Novel injectable solutions of chitosan from biodegradable gels in situ. Biomaterials, 2000: 2155-2161.

Chenite, et al., Rheological characterization of thermogelling chitosa/glycerophosphate solutions. Carbohydrate Polymers, 2001. 46: 39-47.

Cho & Heuzey, Dynamic scaling for gelation of a thermosensitive chitosan-βglycerophosphate hydrogel. Colloid Polymer Science, 2008. 286: 427-434.

Cho, et al., Physical Gelation of Chitosan in the Presence of β-Glycerophosphate: The Effect of Temperature. Biomacromolecules 2005. 6: 3267-3275.

Kempe, et al., Characterization of Thermosensitive chitosan based hydrogels by rheology and electron paramagnetic resonance spectroscopy. Eur J of Pharm and Biopharm, 2008. 68; 26-33.

Molinaro, et al. Biocompatibility of thermosensitive chitosan-based hydrogels: an in vivo experimental approach to injectable biomaterials. Biomaterial, 2002. 23: 2717-2722.

Nasseri, Effect of cholesterol and temperature in the elastic properties of niosomal membranes. International Journal of Pharmaceuticals, 2005. 300: 95-101.

(56) References Cited

OTHER PUBLICATIONS

Parthasarathi, et al., Niosome Encapsulated of Vincristine Sulfate: Improved Anticancer Activity with Reduced Toxicity in Mice. J of Drug Target, 1994. 2(2): 173-183.
Peppas, Polymers in controlled drug delivery. Med Plastics and Biomat Magazine. 1997.
Ruel-Gariepy, et al., A Thermosensitive Chitosan-Based Hydrogel for the Local Delivery of Paclitaxel. Eur J of Pharm and Biopharm, 2004. 57(53-63).
Ruel-Gariepy & Leroux, In Situ-Forming Hydrogels—Review of Temperature-Sensitive Systems. Eur J of Pharm and Biopharm, 2004. 58: p. 409-426.
Ruel-Gariepy, et al., Characterization of Thermosensitive Chitosan Gels for the Sustained Delivery of Drugs. International Journal of Pharmaceutics, 2000. 203: 89-98.
Ta, et al., Injectable chitosan hydrogels for localized cancer therapy. J Controlled Release, 2008. 126: 205-216.
Uchegbu & Vyas, Non-ionic Surfactant Based Vesicles (Niosomes) in Drug Delivery. International Journal of Pharmaceutics, 1998. 172: 33-70.
Uchegbu & Florence, Non-ionic Surfactant Vesicles (Niosomes): Physical and Pharmaceutical Chemistry. Advances in Colloidal and Interface Science, 1995. 58: 1-55.
Zhou, et al., Effect of molecular weight and degree of deacetylation on the preparation and characteristics of chitosan thermosensitive hydrogel as a delivery system. Carbohydrate Polymers, 2008. 73: 265-273.
Costas, et al., Tumor-targeted chlorotoxin-coupled nanoparticles for nucleic acid delivery to glioblastoma cells: a promising system for glioblastoma treatment. Mol Ther Nucleic Acids. Jun. 18, 2013;2:e100.
Deshane, et a., Chlorotoxin Inhibits Glioma Cell Invasion via Matrix Metalloproteinase-2. J Biol Chem. Feb. 7, 2003;278 (6):4135-44. Epub Nov. 25, 2002.
Korch, et al., DNA profiling analysis of endometrial and ovarian cell lines reveals misidentification, redundancy and contamination. Gynecol Oncol. Oct. 2012;127(1):241-8.
Lewis & Garcia, Therapeutic potential of venom peptides. Nat Rev Drug Discov. Oct. 2003;2(10):790-802.
Manosroi, et al., Characterization of vesicles prepared with various non-ionic surfactants mixed with cholesterol. Colloids and Surfaces: Biointerfaces, 2008. 30: 129-138.
Ruel-Gariepy, et al., Thermosensitive Chitosan-Based Hydrogel Containing Lipsomes for the Delivery of Hydrophilic Molecules. J of Controlled Release, 2002. 82: 373-383.
Lakshmi, P.K. et al. Clinical Management of Psoriasis Using 0.25% Niosmal Methotrexate Gel: A Placebo Controlled Double Blind Study. The Internet Journal of Dermatology, 2005. vol. 3, No. 1.
Israelachvili, Intermolecular and Surface Forces: With Applications to Colloidal and Biological Systems, Orlando: Academic Press, 1985, 366-394.
Manosroi, Aranya et al. Characterization of vesicles prepared with various non-ionic surfactants mixed with cholesterol. Colloids and Surfaces B: Biointerfaces 30 (2003), 129-138.
Chitosan—Wikipedia, Jan. 5, 2010. http://en.wikipedia.org/wiki/Chitosan.
Chitosan @ 3Dchem.com, Jan. 5, 2010. http://www.3dchecm.com/molecules.asp?ID=444.
Chitosan—Substance Summary (SID 75560971). PubChem Substance, Jan. 5, 2010. http://pubchem.ncbi.nlm.nih.gov/summary/summary.cgi?sid-75560971&loc=es rss.
Dekkar, M. 1999. NetLibrary—Online Reader: eContect Pane, Jul. 12, 2010. http:netlibrary.com/Reader/EbookPane.aspx, 272-280.
Alpha-glycerophosphoric acid—Substance Summary (SID 148805). PubChem Substance, Jan. 5, 2010. http://pubchem.ncbi.nlm.nih.gov/summary/summary.cgi?sid=148805&loc=es rss.
Quemeneur, Francois et al. Large and Giant Vesicles "Decorated" with Chitosan: Effects of pH, Salt or Glucose Stress, and Surface Adhesion. Biomacromolecules 2007, 8, 2512-2519.
Graham, N.B. Poly(Ethylene Glycol) Gels and Drug Delivery. Poly(Ethylene Glycol) Chemistry. Chapter 17, p. 264-281. New York.London: Plenum Press, 1992.
Lakshmi, P.K. et al. Niosomal methotrexate gel in the treatment of localized psoriasis: Phase I and Phase II studies. Indian J. Dermatol Venereol Leprol 2007:73:157-61.
Mansouri, Sania et al. Chitosan-DNA nanoparticles as non-viral vectors in gene therapy: strategies to improve transfection efficacy. European Journal of Pharmaceutics and Biopharmaceutics 57 (2004) 1-8.
G6376 Beta-Glycerophosphate disodium salt hydrate. Sigma-Aldrich Co., Aug. 6, 2015. http://www.sigmaaldrich.com/catalog/product/sigma/g6376?lang=en&region=US.
Zhang, Liangfang et al. Co-Delivery of Hydrophobic and Hydrophilic Drugs from Nanoparticle-Aptamer Bioconjugates. ChemMedChem 2007, 2, 1268-1271.
Balasubramanian, Sathyamangalam V. and Robert M. Straubinger. Taxol-Lipid Interactions: Taxol-Dependent Effects on the Physical Properties of Model Membranes, Biochemistry 1994, 33, 8941-8947.
http://www.australianprescriber.com/magazine/22/4/88/90/, last accessed Jun. 3, 2016.
Dardevet, et al., Chlorotoxin: a helpful natural scorpion peptide to diagnose glioma and fight tumor invasion. Toxins (Basel) Mar. 27, 2015;7(4):1079-101.

* cited by examiner

ENHANCED TARGETED DRUG DELIVERY SYSTEM VIA CHITOSAN HYDROGEL AND CHLOROTOXIN

FIELD OF INVENTION

This invention relates to drug delivery systems. Specifically, the invention relates to controlling the release rate of a therapeutic drug using nanoparticle vesicles associated with chlorotoxin and embedded in hydrogel networks.

BACKGROUND OF THE INVENTION

Various drug delivery systems have been developed to lessen the toxicity and improve the efficacy of drugs. Antineoplastic and anti-cancer agents are of particular concern, due to the high cellular toxicity inherent in many of these drugs.

Ovarian Cancer is the fourth leading cause of death by cancer in women (ca. 15280 deaths in 2007 in the United States) (Greenlee, et al., *Cancer Statistics*, 2005. CA Cancer J Clin 2005; 51:15-36; Jemal, A., A. Thomas, T. Murray, and M. Thun, *Cancer Statistics*, 2002. CA: A Cancer Journal for Clinicians, 2002. 52: p. 23-47), the leading cause of death from gynecologic malignancies and the second most commonly diagnosed gynecologic malignancy. Ovarian cancer detection in the early stages is difficult because most women show little to no symptoms until the cancer has progressed to an advanced stage and become difficult to treat, with the relative survival rate at a low 46% (Greenlee et al., *Cancer Statistics*, 2005. CA Cancer J Clin 2005; 51:15-36; Schwartz P E, Taylor K J. *Is early detection of ovarian cancer possible?* Ann Med 1995; 27:519-28). Surgery is the first step in the treatment and is frequently necessary for diagnosis, as seen in FIG. 1. Chemotherapy is typically administered after surgery to treat any residual tumors. The traditional chemotherapeutic administration techniques include intravenous (IV) injection of the drugs directly into the blood stream (Armstrong, D. K., et al., *Intraperitoneal cisplatin and paclitaxel in ovarian cancer*. New England Journal of Medicine, 2006. 354(1): p. 34-43; Markman, et al., *Combination Intraperitoneal Chemotherapy with Cisplatin, Cytarabine, and Doxorubicin for Refractory Ovarian-Carcinoma and Other Malignancies Principally Confined to the Peritoneal-Cavity*. J Clin Oncol, 1984. 2(12): p. 1321-1326). This technique has been used in the past years and has been successful in containing the spread of tumors and hence treating many types of cancer. Since it is not localized it exposes the whole body to the chemotherapy drugs. Hence, apart from destroying tumor cells they also attack normal healthy cells (Markman, et al., *Combination Intraperitoneal Chemotherapy with Cisplatin, Cytarabine, and Doxorubicin for Refractory Ovarian-Carcinoma and Other Malignancies Principally Confined to the Peritoneal-Cavity*. J Clin Oncol, 1984. 2(12): p. 1321-1326) resulting in extensive side effects.

Surgery is the first step in the treatment of cancerous tumors at early localized or intermediate stage, with chemotherapy used after surgery to treat any residual tumors. However, adjuvant chemotherapy suffers from non-specific distribution of drugs, and typically has severe side effects. Further, most chemotherapeutic drugs has low bioavailability, requiring multiple administrations, and therefore significantly increase the costs associated with treatment.

Conventional techniques to prevent cancer recurrence include intraperitonial chemotherapy. Drugs are delivered directly into the intraperitonial cavity (Armstrong, et al., *Intraperitoneal cisplatin and paclitaxel in ovarian cancer*. New Eng J of Med, 2006. 354(1): p. 34-43) using a catheter, but also presents challenges. Tumors in the abdominal cavity are exposed to higher concentrations of drug for longer periods of time, resulting in increased hematologic, metabolic and neurologic toxicity (Armstrong, et al., *Intraperitoneal cisplatin and paclitaxel in ovarian cancer*. New Eng J of Med, 2006. 354(1): p. 34-43; Markman et al., *Combination Intraperitoneal Chemotherapy with Cisplatin, Cytarabine, and Doxorubicin for Refractory Ovarian-Carcinoma and Other Malignancies Principally Confined to the Peritoneal-Cavity*. Journal of Clinical Oncology, 1984. 2(12): p. 1321-1326; Hamilton &. Berek, *Intraperitoneal chemotherapy for ovarian cancer*. Curr Opinion in Oncol, 2006. 18(5): p. 507-515). Also, the catheters may become plugged over time (Hamilton & Berek, *Intraperitoneal chemotherapy for ovarian cancer*. Curr Opinion in Oncol, 2006. 18(5): p. 507-515) leading to infections and other complications. Moreover, this technique is available only to select patients with minimal residual tumors (Gore, et al., *Intraperitoneal chemotherapy in ovarian cancer remains experimental*. J Clin Oncol, 2006. 24(28): p. 4528-4530).

Localized delivery systems provide an alternative approach to chemotherapy, allowing for direct delivery to specific targeted sites. Moreover, localized delivery reduced toxicity as less drug is required, can be tailored to provide controlled and prolonged release of drug to the tumor or cancer cells, and reduced or eliminated the need for frequent administration of drug. Accordingly, local delivery provides low cost treatment, especially in comparison to traditional treatment.

Physical encapsulation or liposomes containing neutral or zwitterionic lipids have been used as localized drug delivery systems. The lipids in liposomes arrange themselves into bilayers and entrap one (unilameliar) or more (oligo- or multilamellar) spaces. The spaces between the bilayers of the lipids are usually filled with water. The liposome-encapsulated drugs are entrapped in the internal aqueous space. Conventional liposomes, which rely upon the internal entrapment of the drug, often have difficulty entrapping a high concentration of a drug, as the efficiency depends upon the volume of fluid outside of the liposomes and circumscribed within the internal aqueous vesicular space. During long-term storage, drugs entrapped within liposomes leak from the internal aqueous space into the surrounding milieu, causing the drug to be lost from its desired intra-liposomal location.

Accordingly, what is needed is an improved drug delivery system that allows progressive release of drug over a prolonged period of time.

SUMMARY OF THE INVENTION

As such a localized drug delivery system was developed with niosomes embedded in a chitosan hydrogel with targeting capabilities to provide for a tunable nano-delivery system with chlorotoxin (TNDS-CTX). The system uses niosomes to encapsulate hydrophilic and hydrophobic drugs. Advantageously, niosomes show better stability, easier storage, and lower cost compared to liposomes. The niosomes are embedded in chitosan, a biocompatible and biodegradable material, thereby providing a dual packaging system showing sustained drug release. Moreover, the system can be designed to tailor the themosensitivity of the delivery system. Chitosan also has mucoadhesive properties, allowing for targeted delivery of the drug. Finally, the composition uses chlorotoxin, a 36 Amino Acid Peptide purified from Scorpion Venom (*Leiurus quinquestriatus*), as seen in SEQ ID No. 1, which effects its action through blocking chloride channels of neurons resulting in paralysis. Research identified an interaction between metalloproteinase-2 (MMP-2) isoforms found on glioma cells, showing the toxin binds preferentially to neuroectodermal tumors, e.g., glioma cell surfaces, but not to normal tissues, further allowing for targeted drug delivery (Deshane, et al., Chlorotoxin inhibits glioma cell invasion via matrix metalloproteinase-2. J Biol Chem. 2003 Feb. 7; 278(6) :4135-44).

MCMPCFTTDHQMARKCDDCCGGKGRGKCYGPQ-CLCR (SEQ ID NO. 1).

The niosomes were prepared using Span 60+Cholesterol+ Dicetyl Phosphate. However, other constituents may be used, such as crown ether amphiphiles bearing a steroidal moiety, 1,2-dialkyl glycerol polyoxyethylene ether, hexadecyl poly-5-oxyethylene ether, hexadecyl poly-5-oxyethylene ether ($C_{16}EO_5$); octadecyl poly-5-oxyethylene ether ($C_{18}EO_5$); hexadecyl diglycerol ether ($C_{16}G_2$); sorbitan monopalmitate (Span 40) and sorbitan monostearate (Span 60), Solulan™ C24 (poly-24-oxyethylene cholesteryl ether), polysorbate 20, Span detergents, Brij detergents, such as Brij-35, and polyoxyethylene, and polysorbates. Other components of the niosomes include, cholesterols, and, optionally, negative charged molecules such as dicetyl phosphates, cetyl sulphate, phosphatidic acid, phosphatidyl serine, oleic acid, palmitic acid.

The niosome optionally includes at least one negative charged molecule, such as polyoxyethylene (61), sorbitan monostearate, cetyl sulphate, phosphatidic acid, phosphatidyl serine, oleic acid, palmitic acid, and dicetyl phosphates. In specific embodiments of the drug delivery system, the niosome comprises sorbitan monostearate, at least one cholesterol, and dicetyl phosphate at a ratio of 1:1:0.1. The properties of any niosomal system are determined by hydration of the niosome, the nature of the drug, the composition of the membrane, addition of kinetic energy and/or size reduction (Uchebgu, et al., *Non-ionic surfactant based vesicles* (*niosomes*) *in drug delivery*. Int J Pharm, 1998 Oct. 15; 172(1):33-70). These variables must be carefully controlled during the design and manufacture of a niosomal drug delivery system.

The niosome was prepared using thin film formation, followed by thin film hydration and size reduction via extrusion. Niosomes were separated using ultracentrifugation, and analyzed for size using dynamic light scattering.

Testing was undertaken to determine encapsulation efficiency and the molecules analyzed by Transmission Electron Microscopy (TEM).

The niosomes optionally also include at least one negatively charged molecules, such as polyoxyethylene (61), sorbitan monostearate, cetyl sulphate, phosphatidic acid, phosphatidyl serine, oleic acid, palmitic acid, and dicetyl phosphates. In specific embodiments, the noisome is composed of sorbitan monostearate, cholesterol and dicetyl phosphate combined in the ratio 1:1:(0.1). The niosomes are optionally extruded. Unincorporated hydrophilic drug may be separated from the niosomes by ultracentrifugation.

In addition to forming niosomes for the drug delivery medium, the niosomes are optionally added to a hydrogel, such as chitosan. In specific embodiments, the ratio of niosome to chitosan ratios ranges from (0.15):1 to (0.45):1. The hydrogel of the drug delivery medium is optionally chitosan. In some embodiments, the chitosan has a molecular weight within the range of 19,000 Daltons and 31,000 Daltons. Further, the polymer hydrogel may also include a cross-linking molecule, such as β-glycerophosphate. Other useful cross-linking materials include polyols and/or polyoses. Nonlimiting examples include glycerol, pentaerythritol, ethylene glycol, glycerin, castor oil, sucrose polyethylene glycol, polypropylene glycol, poly(tetramethylene ether) glycol, trehalose, glycogen, cellulose, chitin, amylose, and amylopectin glycogen. In specific embodiments, the β-glycerophosphate is added at a ratio of chitosan to β-glycerophosphate of 4.0:1. The hydrogel also optionally comprise a plurality of biodegradable polymer hydrogel layers, where the niosomes are embedded in the hydrogel layers. In such embodiments, the adjoining hydrogel layers have distinct properties. In embodiments employing a plurality of biodegradable polymer hydrogel layers, the layers may optionally be sandwiched together thereby forming a gradient network to package vesicles in varying microenvironments to tune release rates from an identical population of vesicles wherein adjoining hydrogel layers have distinct properties. The distinct properties of the hydrogel layers may include cross-link density, pH-sensitivity and temperature sensitivity.

The incorporation of niosomes into a chitosan hydrogel has several advantages over each individually being used. First, embedding niosomes in a chitosan hydrogel can yield slower drug release especially for small molecule drugs. Second, chitosan hydrogel may improve the release kinetics of drugs from niosomes by protecting them with an extra barrier, resulting in extended release rates. Third, as a localized delivery system, chitosan hydrogels can prevent the migration of niosomes away from the targeted tumor sites. Finally, chitosan has mucoadhesive property which can be used in the targeting of the tumor cells overexpressing Mucin 1 (MUC1).

To enhance the specific targeting, the capacity of chitosan to target MUC1 overexpression in cancer cells was analyzed. Similarly, the incorporation of chlorotoxin in this system was evaluated, as chlorotoxin preferentially binds to neuroectodermal tumors such as glioma, but not to normal tissue. The overexpression of MUC1, a mucin antigen, in certain cancer cells has been used as an attractive therapeutic target in the design of a drug delivery system consisting of chitosan with a distinct mucoadhesive property. To determine the level of MUC1 expression in different cell lines, Cell based Enzyme Linked Immunosorbent Assay (Cell ELISA) was used. Attenuated Total Reflectance-Fourier Transform Infra-Red (ATR-FTIR) Spectroscopy was used to investigate the possible molecular interaction between chitosan hydrogel and various cell lines. ATR-FTIR spectroscopy was also applied to determine binding interactions of chlorotoxin to the surface of different cell lines. It is expected to understand the fundamental mechanisms that govern localized drug delivery and use such knowledge to design a controllable and flexible drug delivery system for the treatment of cancer The present invention features specific targeted drug delivery to tumor cells through mucoadhesive chitosan and chlorotoxin.

BRIEF DESCRIPTION OF THE DRAWINGS

For a fuller understanding of the invention, reference should be made to the following detailed description, taken in connection with the accompanying drawings, in which:

FIG. 1 is a graph summarizing standard clinical breast cancer treatment.

FIG. 2 is a chemical structural diagram depicting exemplary vesicle-forming crown ethers of a cholestanyl derivative.

FIG. 3 is a chemical structural diagram depicting exemplary vesicle-forming crown ethers of a cholesteryl derivative.

Figure 7:
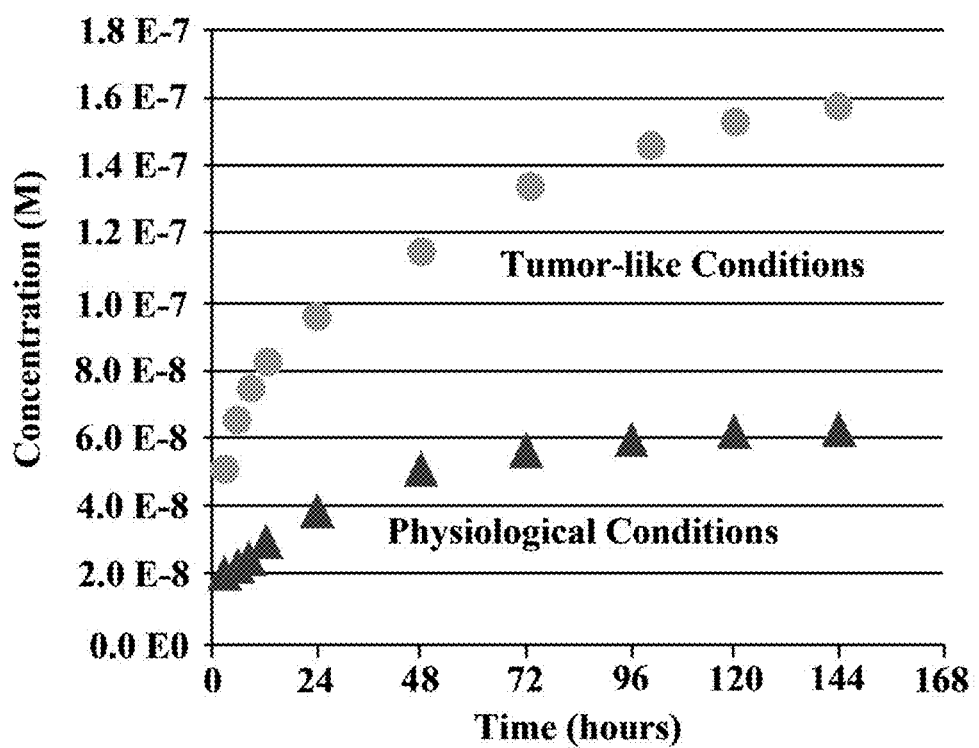

FIG. 7 is a graph showing release rate studies for the niosomes in vitro for 5(6)-carbofluorescein dye. Tumor-like conditions (circles) were tested in salt-free water at a pH of 6, while physiological conditions (triangles) were tested in 1×PBS at a pH of 7.4. The conditions were established as niosomes are osmotically active, and susceptive to rupture depending on the tonicity of surrounding environment. PBS provides a more stable environment, whereas salt-free water causes an increase in the osmotic pressure resulting in faster release rates).

Figure 8:
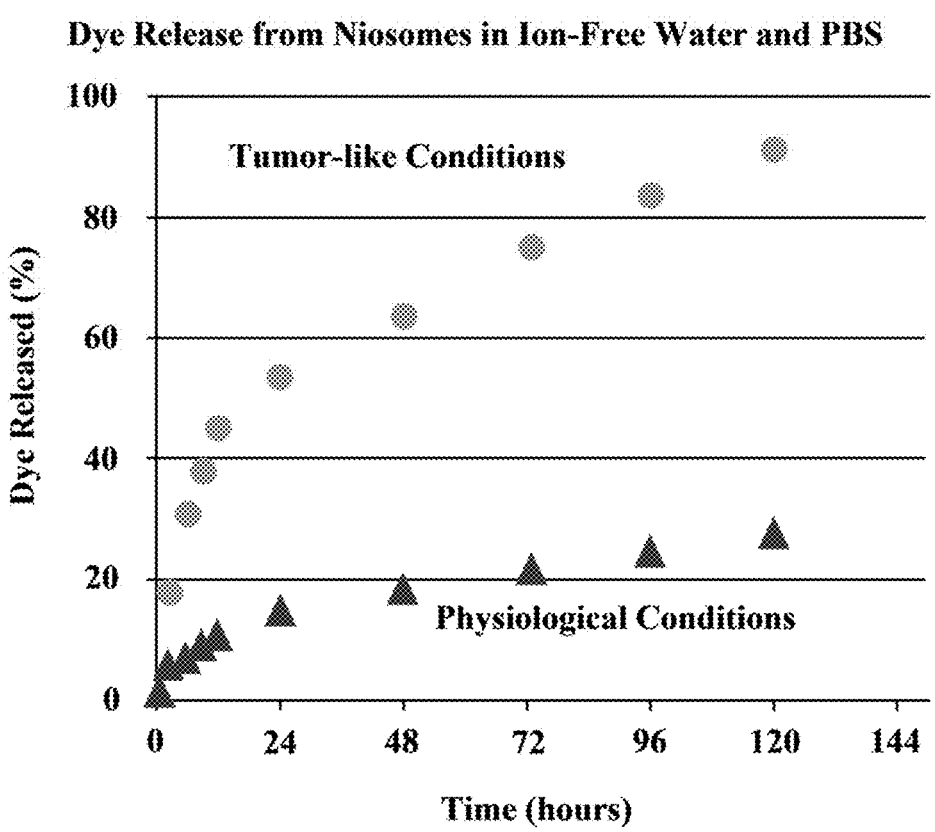

FIG. 8 is a graph showing release rate studies for the niosomes in vitro for 5(6)-carbofluorescein dye. Tumor-like conditions (circles) were tested in salt-free water at a pH of 6, while physiological conditions (triangles) were tested in 1×PBS at a pH of 7.4. The conditions were established as niosomes are osmotically active, and susceptive to rupture depending on the tonicity of surrounding environment. PBS provides a more stable environment, whereas salt-free water causes an increase in the osmotic pressure resulting in faster release rates).

Figure 9:
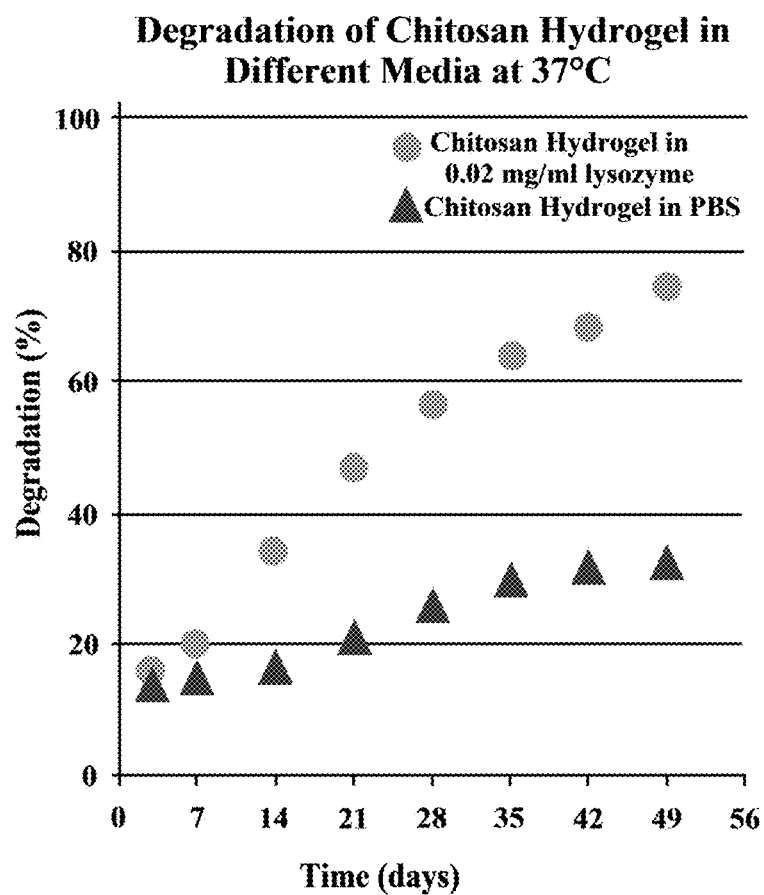

FIG. 9 is a graph showing degradation patterns of chitosan hydrogel at 37° C. Chitosan was subjected to 1×PBS or 0.02 mg/ml lysozyme in 1×PBS.

Figure 10:
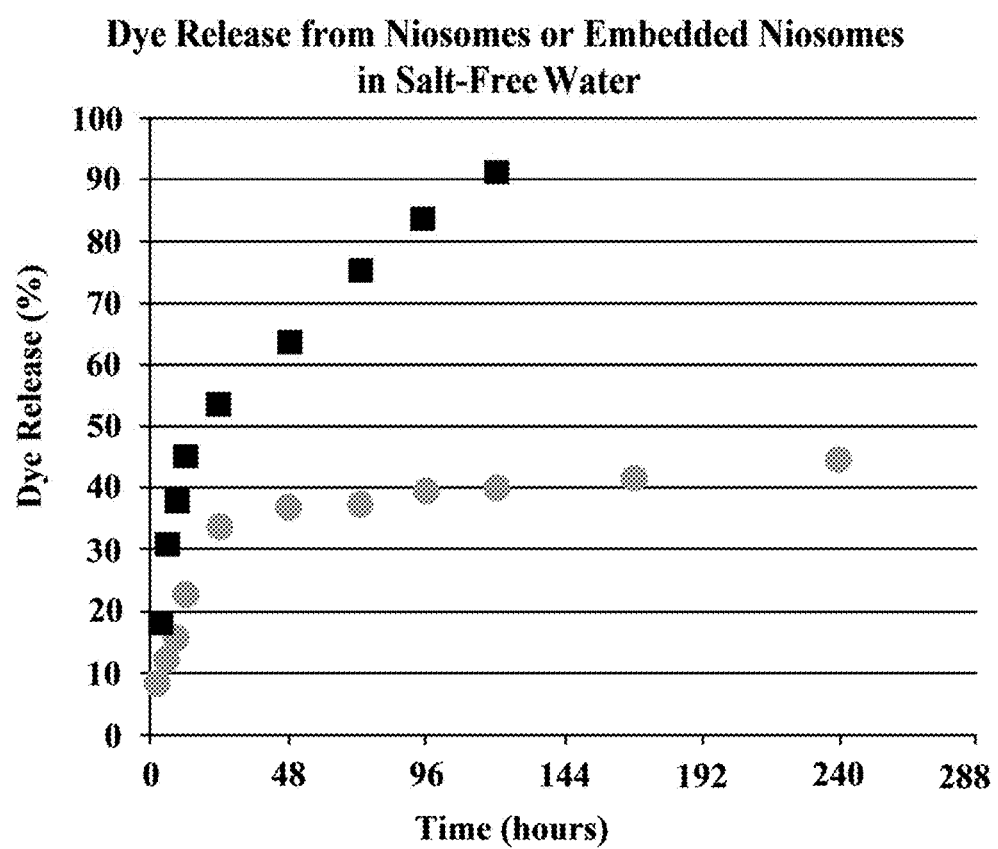

FIG. 10 is a graph showing release rates for niosomes embedded in a chitosan hydrogel compared to non-embedded (free) niosomes, in vitro in salt-free water. Release rates of 5(6)-carbofluorescein dye in bare noisome (squares) and Niosomes in chitosan (circles) were tested in salt-free water at a pH of 6.

Figure 11:
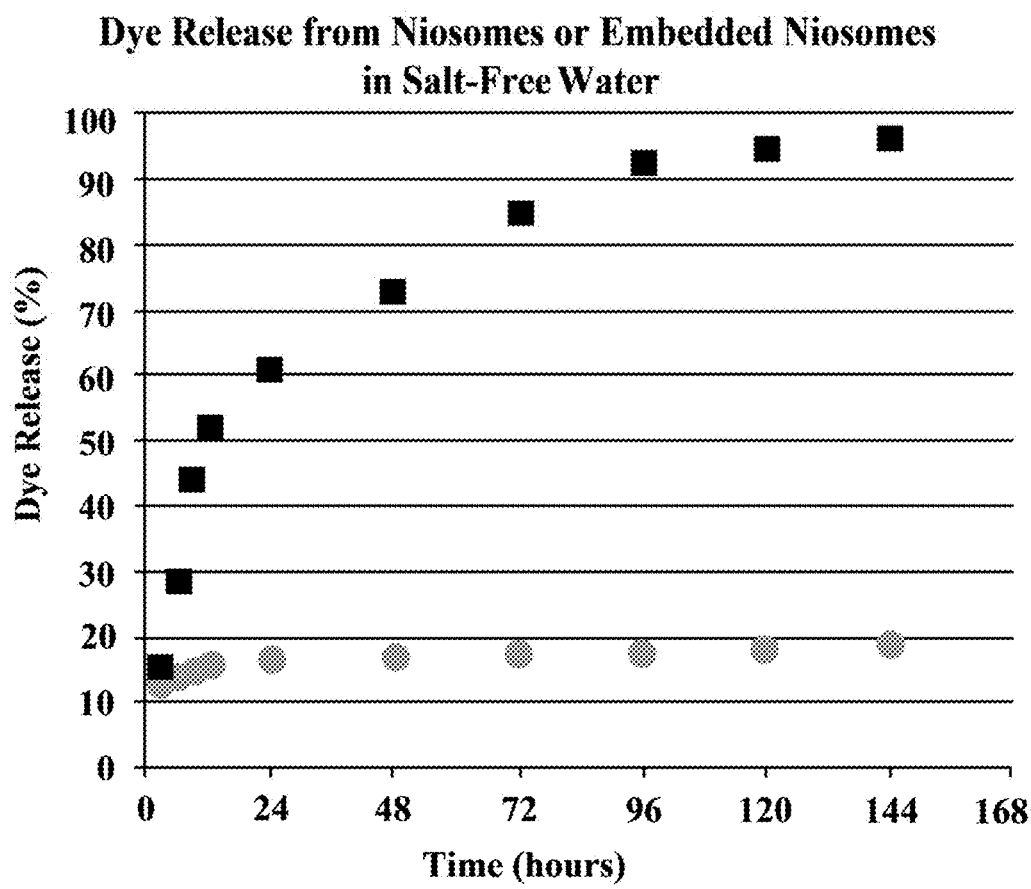

FIG. 11 is a graph showing release rates for niosomes embedded in a chitosan hydrogel compared to non-embedded (free) niosomes, in vitro in salt-free water. Release rates of 5(6)-carbofluorescein dye in bare noisome (squares) and niosomes embedded in chitosan (circles) were tested in salt-free water at a pH of 6.

Figure 12:
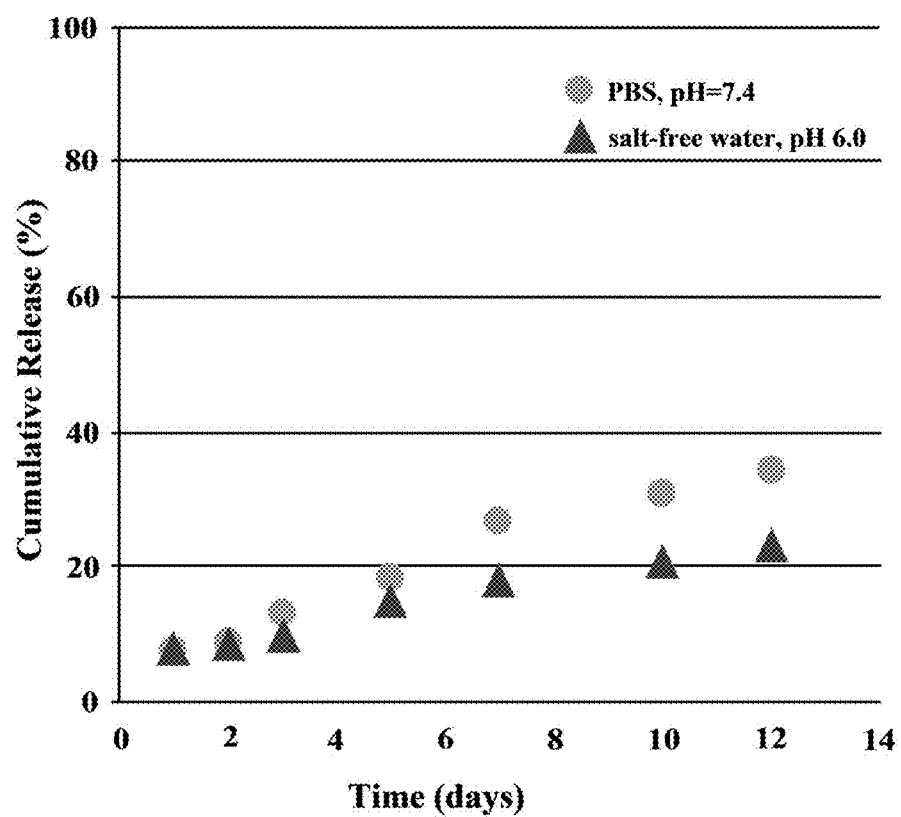

FIG. 12 is a graph showing release rates of paclitaxel loaded in niosomes embedded in a chitosan hydrogel in vitro in salt-free water, pH 6 (square) or 1×PBS, pH 7.4 (circle).

Figure 13:
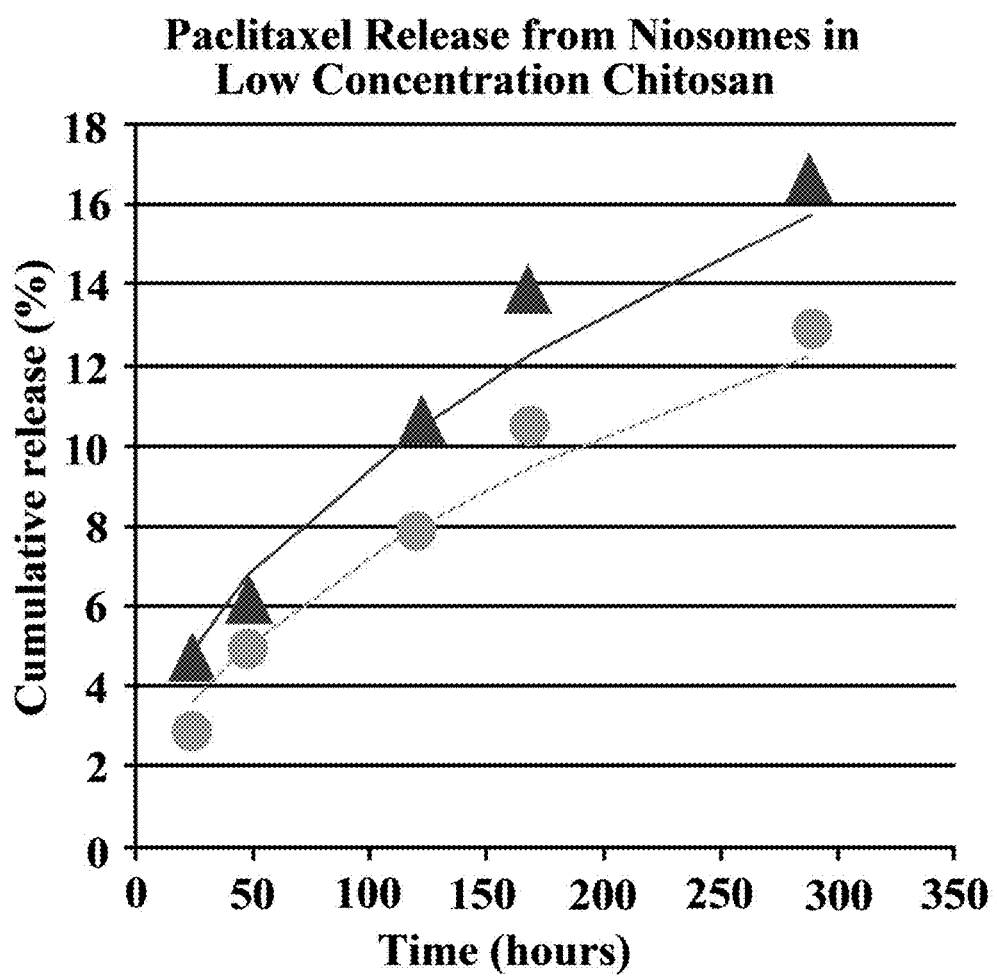

FIG. 13 is a graph showing paclitaxel release rates for low concentration chitosan with embedded niosomes (L-Ch Nio) in PBS at a pH of 7.4 (triangle) and pH of 6.3 (circle). The predicted release rates for pH 7.4 (solid dark gray line) and 6.4 (dashed light gray line) from modeling are shown.

Figure 14:
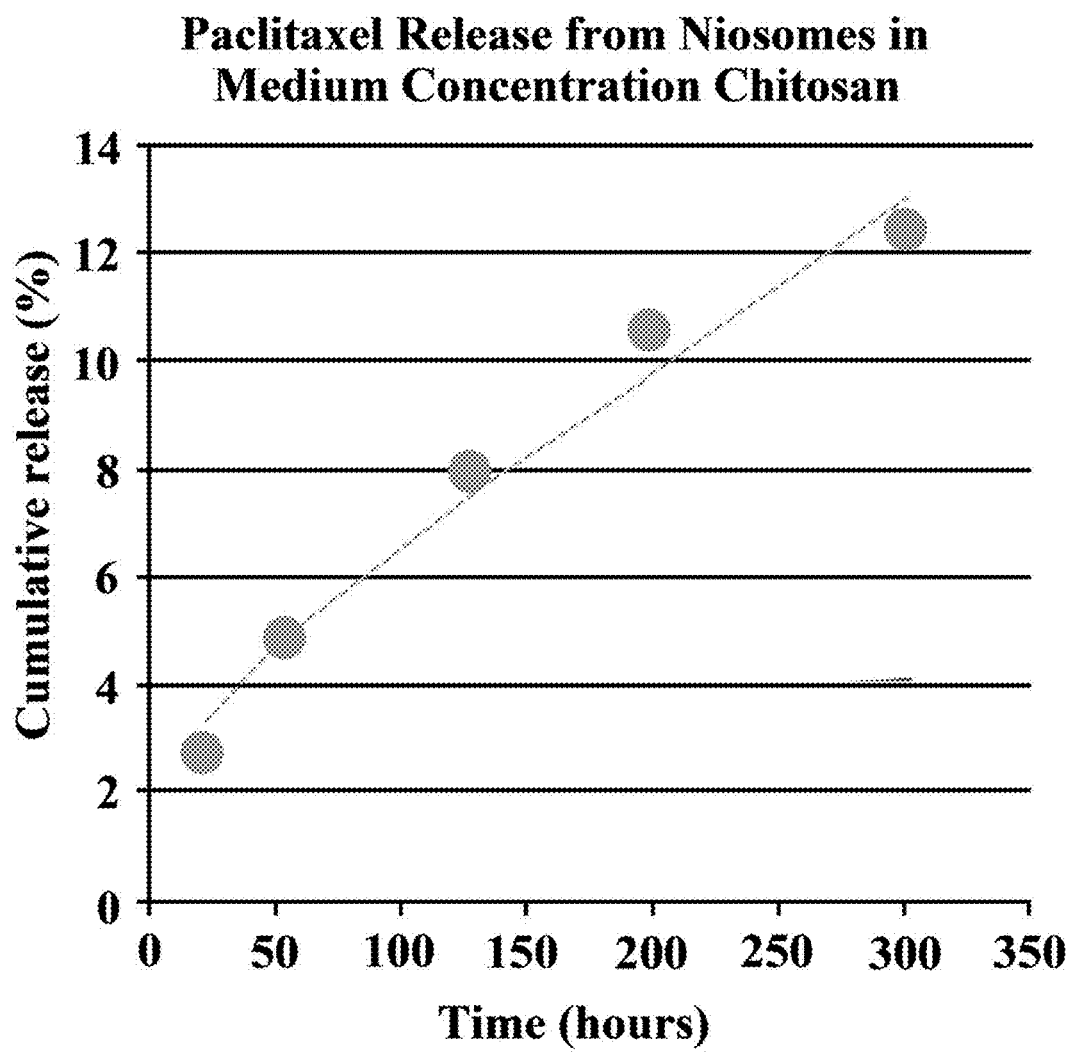

FIG. 14 is a graph showing paclitaxel release rates for medium concentration chitosan with embedded niosomes (M-Ch Nio) in PBS at a pH of 6.3. The predicted release rates for pH 6.4 (dashed line) from modeling is shown.

Figure 15:
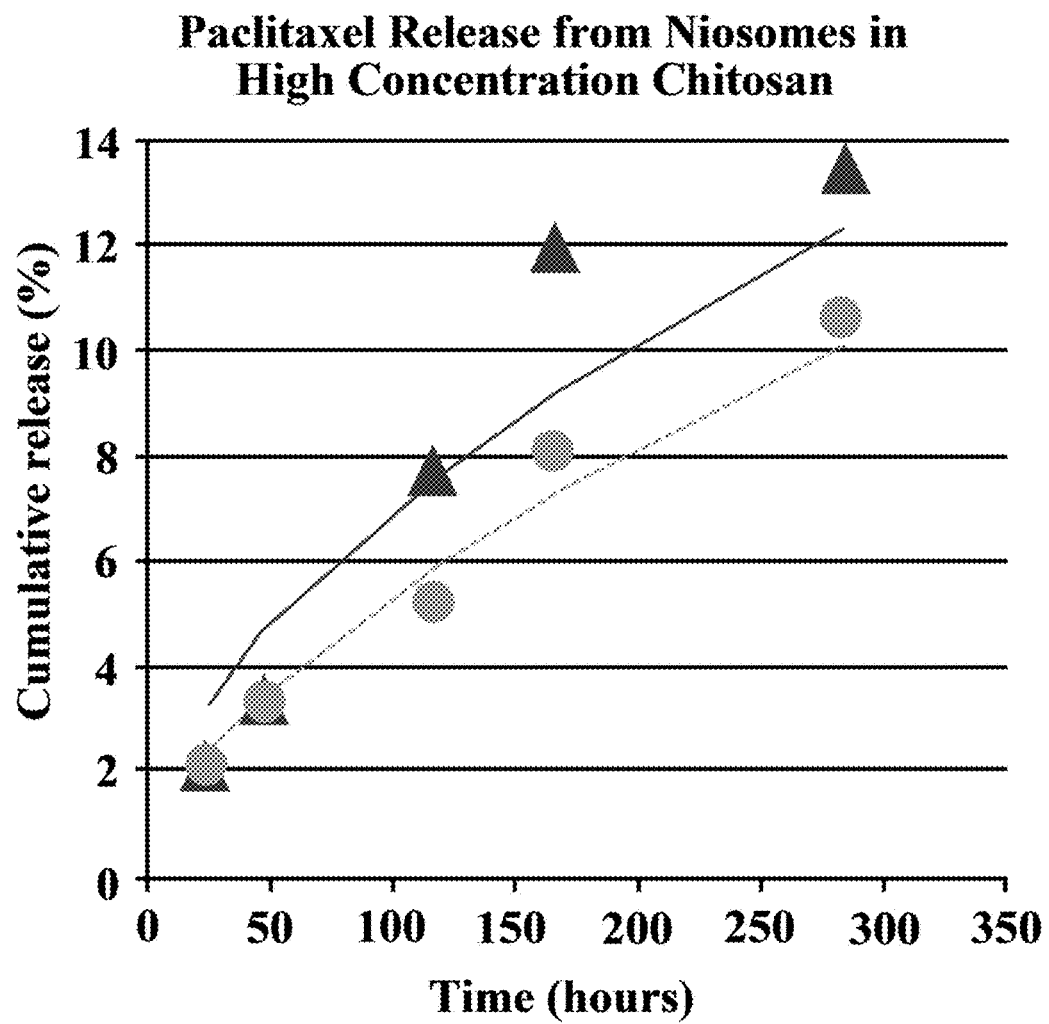

FIG. 15 is a graph showing paclitaxel release rates for high concentration chitosan with embedded niosomes (H-Ch Nio) in PBS at a pH of 7.4 (tringal) and pH of 6.3 (circle). The predicted release rates for pH 7.4 (solid dark gray line) and 6.4 (dashed light gray line) from modeling are shown.

Figure 16:
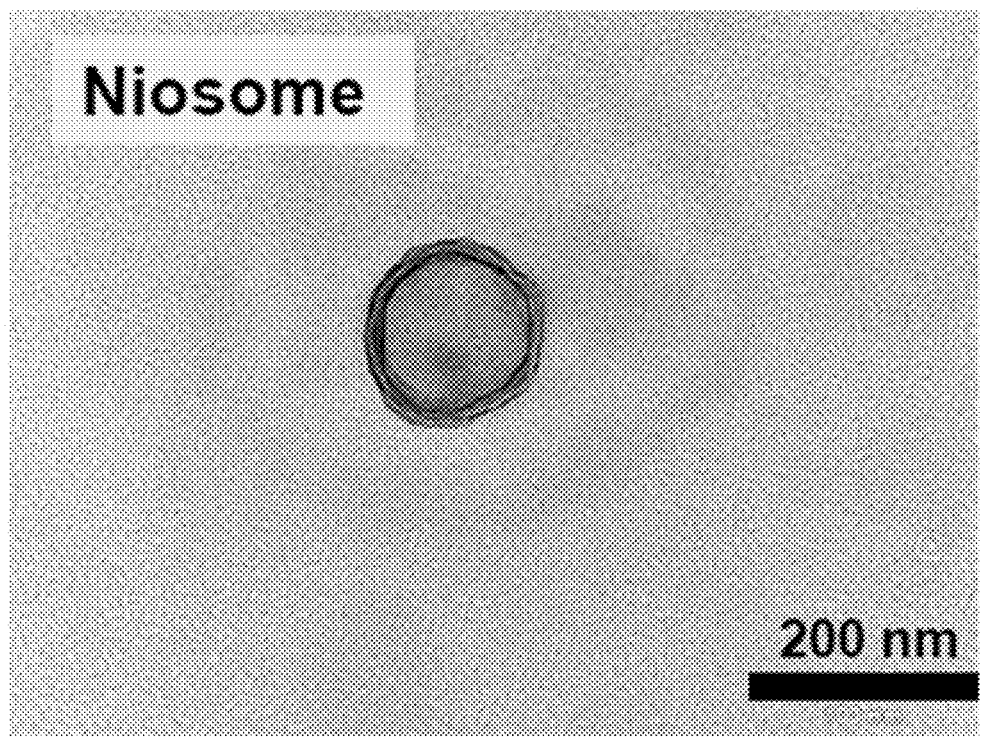

FIG. 16 is a transmission electron microscope image of an exemplary niosome.

Figure 17:
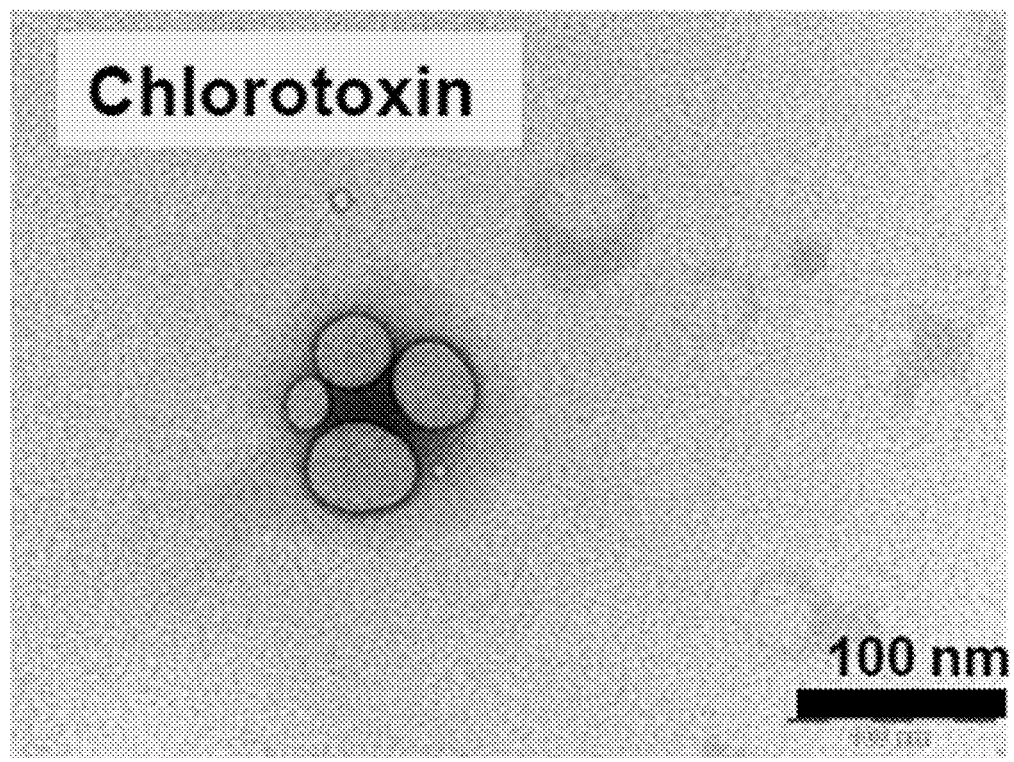

FIG. 17 is a transmission electron microscope image of chlorotoxin protein.

Figure 18:
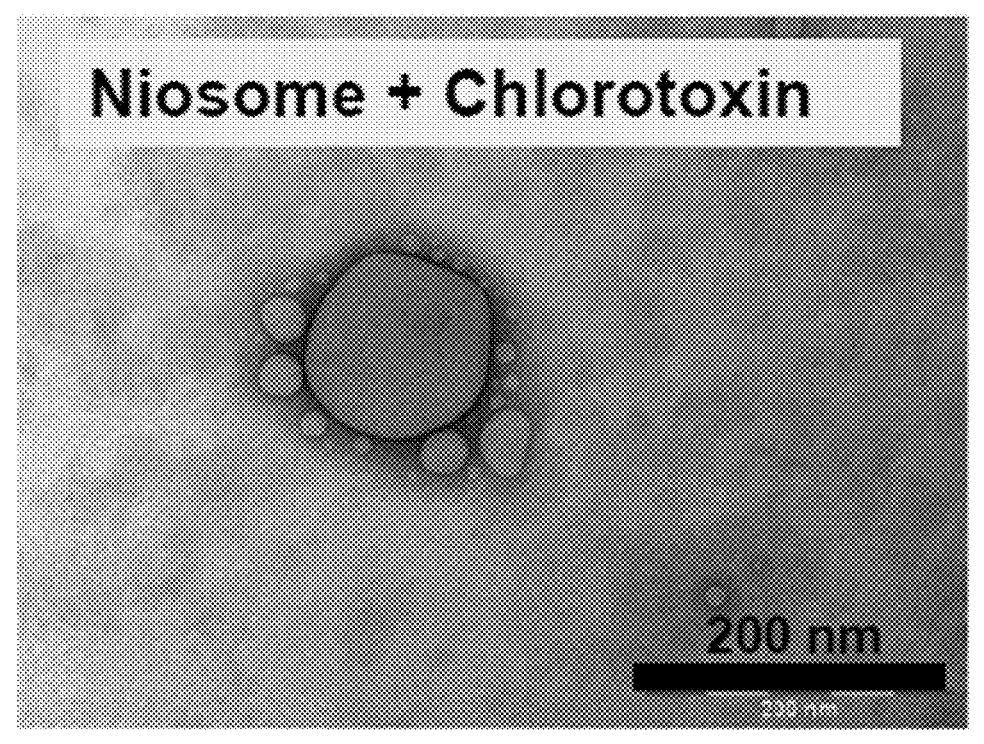

FIG. 18 is a transmission electron microscope image of a niosome associated with CTX.

Figure 19:
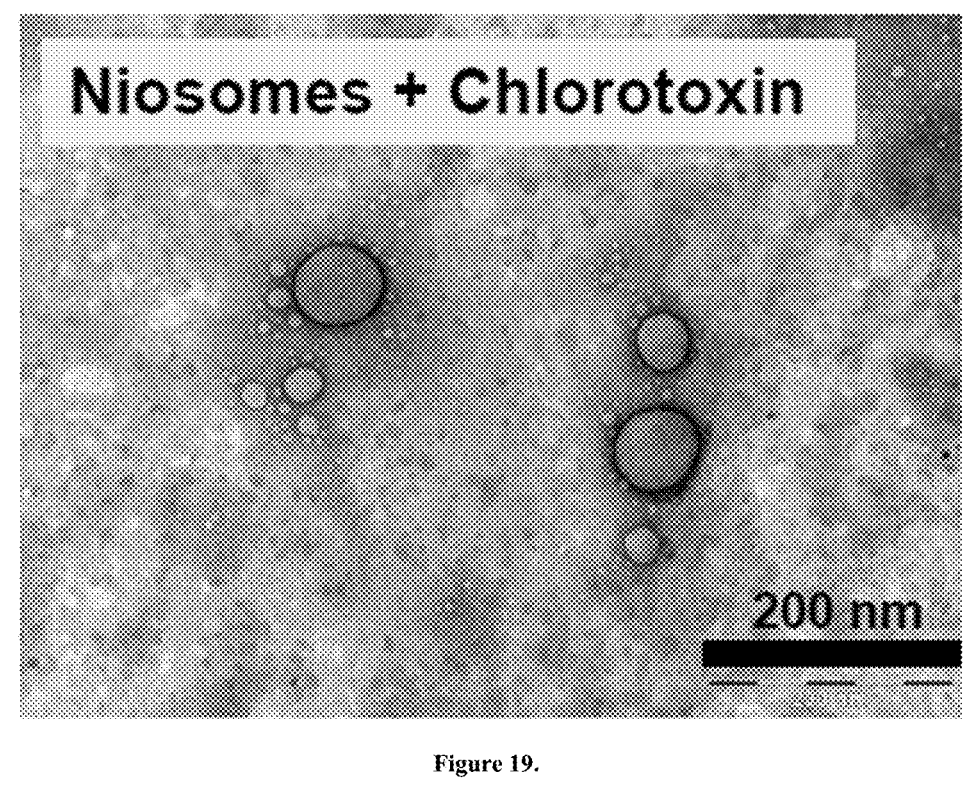

FIG. 19 is a transmission electron microscope image of a plurality of niosomes associated with CTX.

Figure 20:
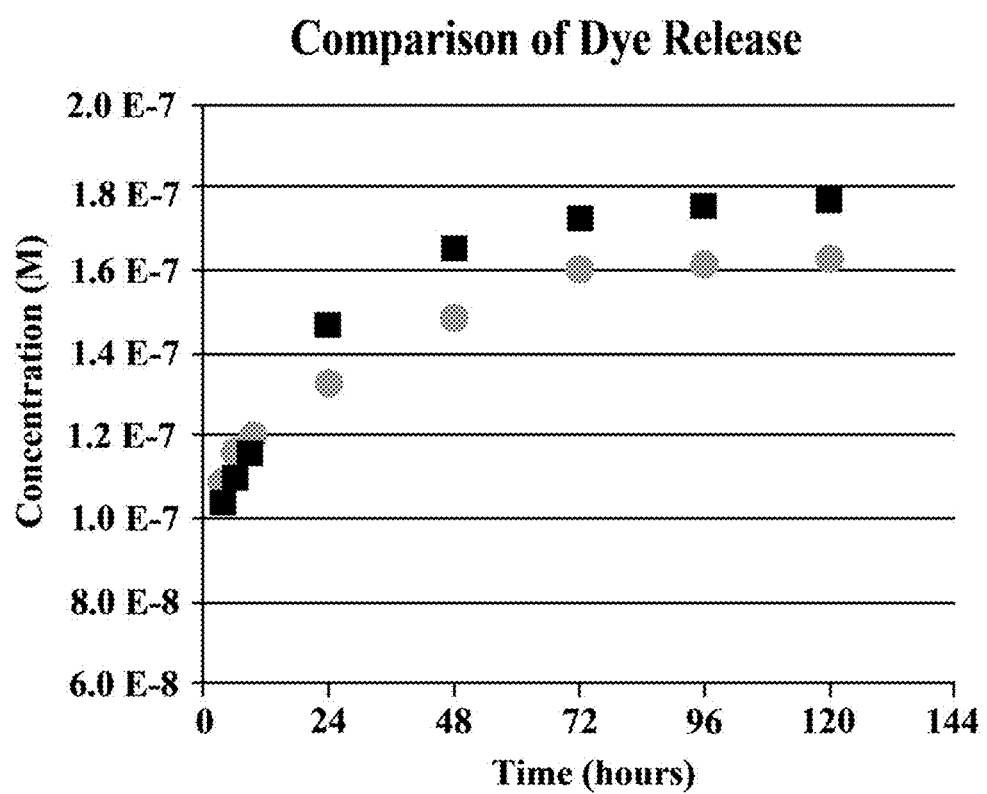

FIG. 20 is a graph showing release rates for CTX-associated niosomes embedded in a chitosan hydrogel compared to niosomes embedded in chitosan-only hydrogel, in vitro. Niosomes in chitosan (squares) and niosomes with CTX in chitosan (circles) were tested to determine the concentrations of dye released from the niosomes.

Figure 21:
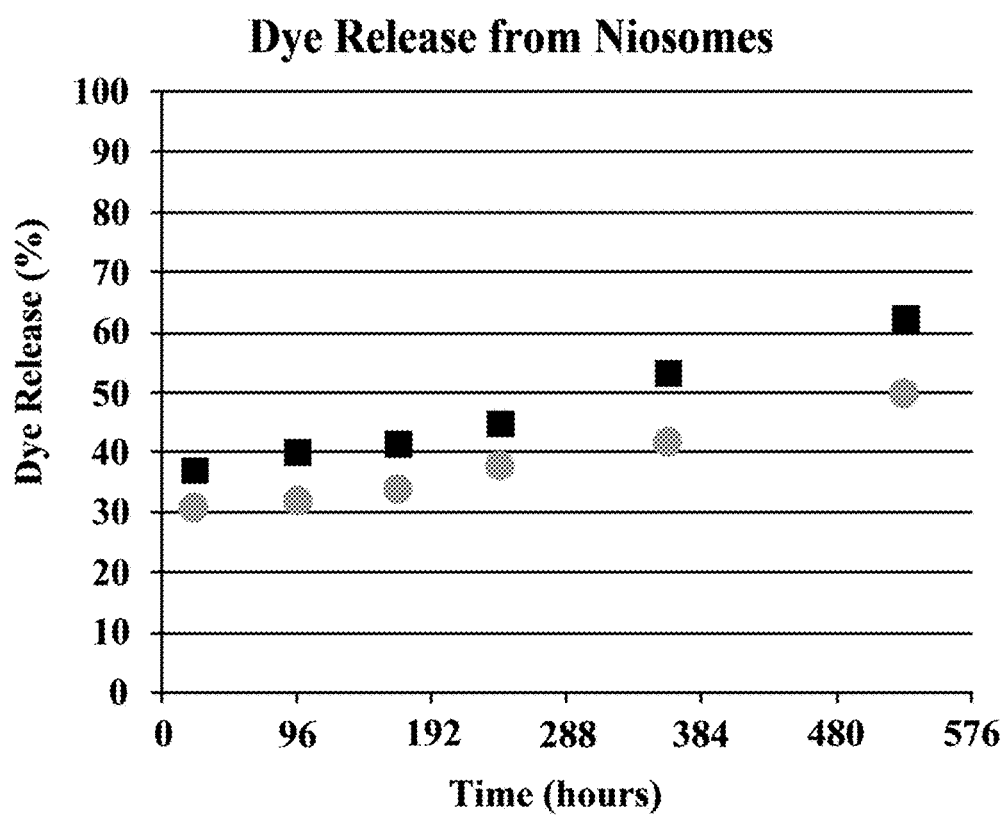

FIG. 21 is a graph showing release rates for CTX-associated niosomes embedded in a chitosan hydrogel compared to niosomes embedded in chitosan-only hydrogel, in vitro. Niosomes in chitosan (squares) and Niosomes with CTX in chitosan (circles) were tested in salt-free water to determine the concentrations of dye released from the niosomes. The inclusion of CTX slightly extends the drug release rate of embedded niosomes.

Figure 22:
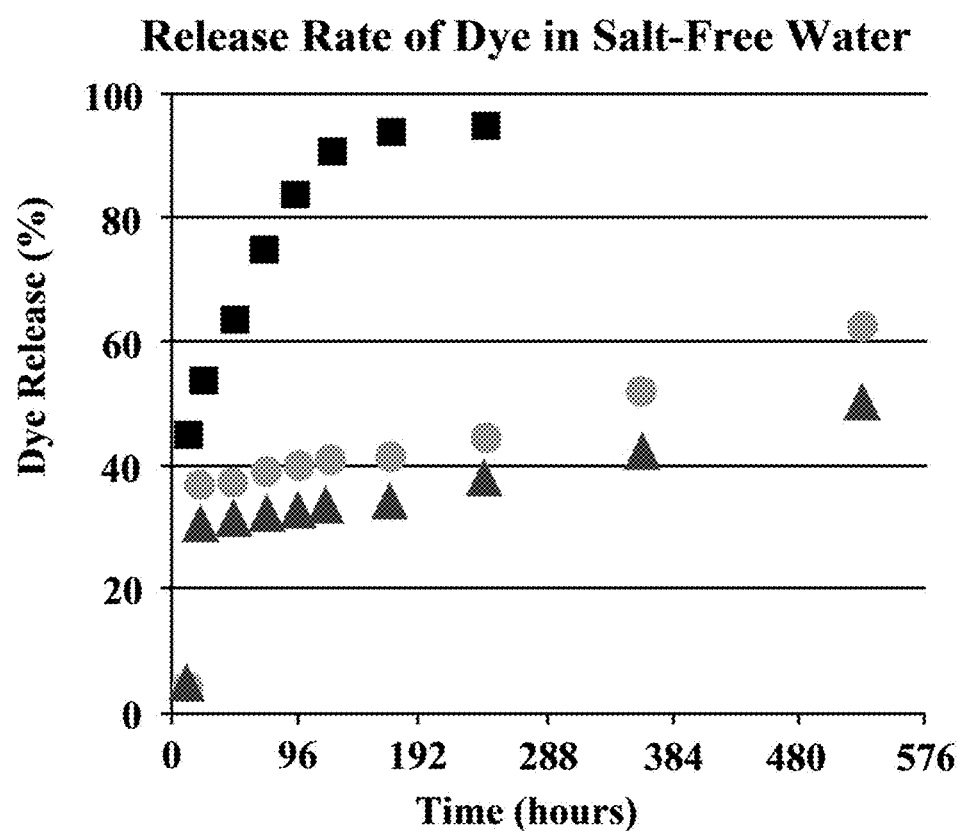

FIG. 22 is a graph showing release rates for bare niosomes versus CTX-associated niosomes embedded in a chitosan hydrogel compared to niosomes embedded in chitosan-only hydrogel, in vitro. Bare noisome (squares), niosomes in chitosan (circles) and noisome with CTX in chitosan (triangles) were tested in salt-free water at a pH of 6 to determine the concentrations of 5(6)-carbofluorescein dye released from the niosomes.

Figure 23:
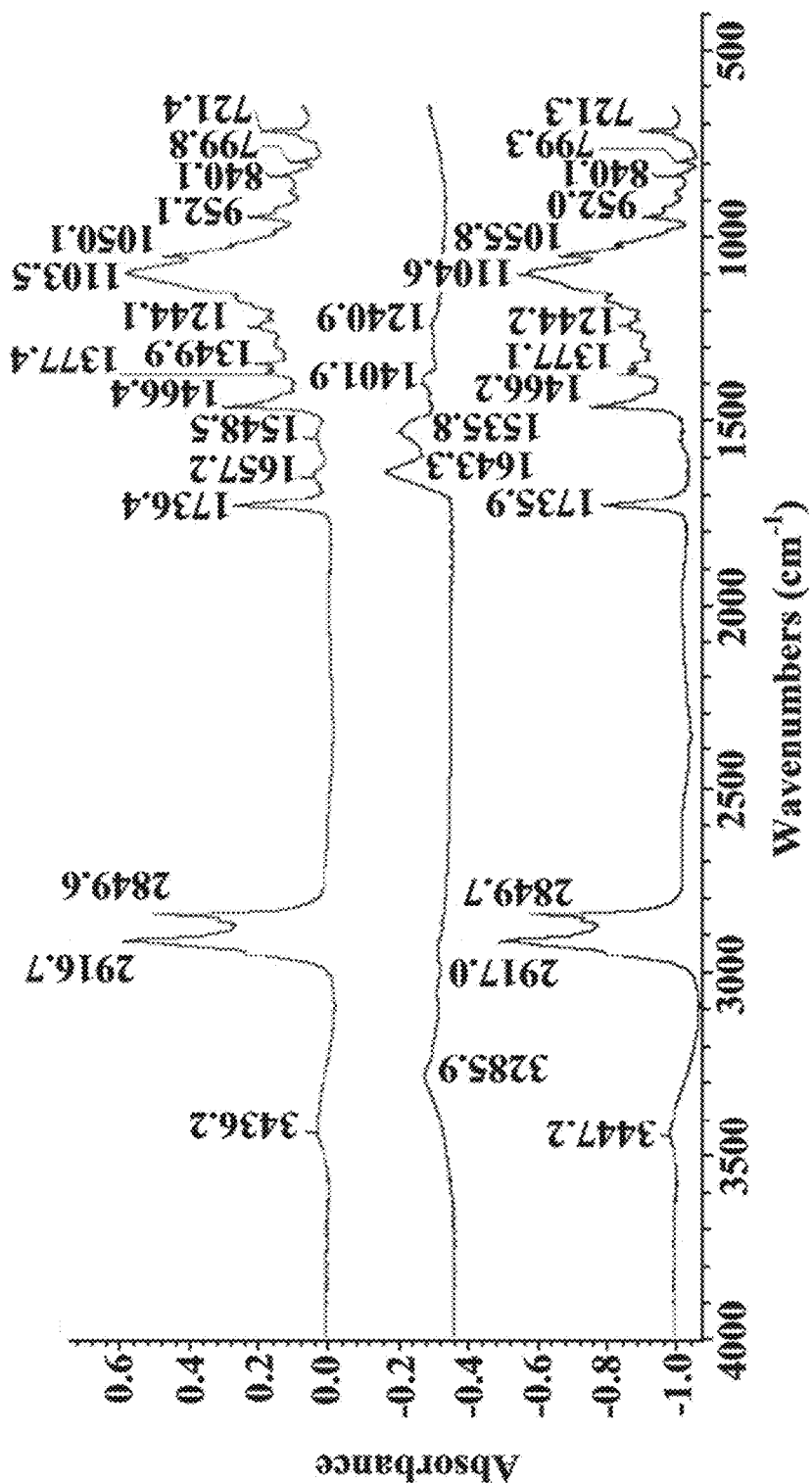

FIG. 23 is a trace of comparative ATR-FTIR spectra of niosomes (bottom trace), chlorotoxin, i.e. CTX, (middle trace), and a combination of chlorotoxin and niosomes (top trace).

Figure 24:
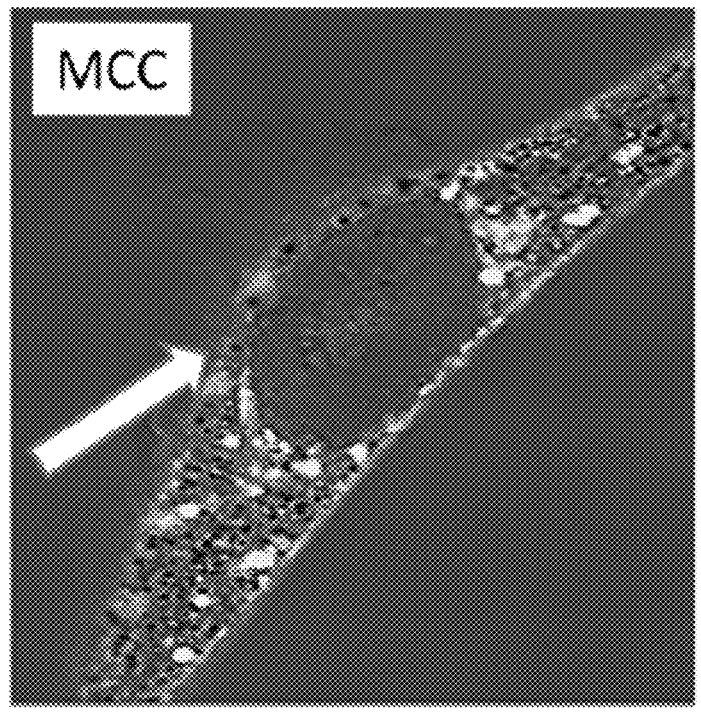

FIG. 24 is a confocal microscope image of MCC3 cells exposed only to chitosan. Images were stained with wheat agglutinin/fluorescence of the cell membrane.

Figure 25:
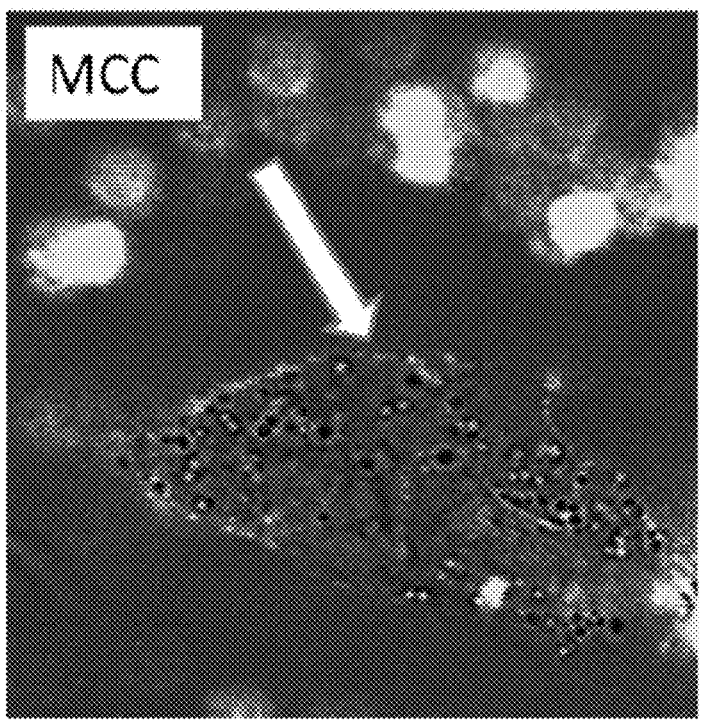

FIG. 25 is a confocal microscope image of MCC3 cells targeted by the delivery system, images were stained with wheat agglutinin/fluorescence of the cell membrane.

Figure 26:
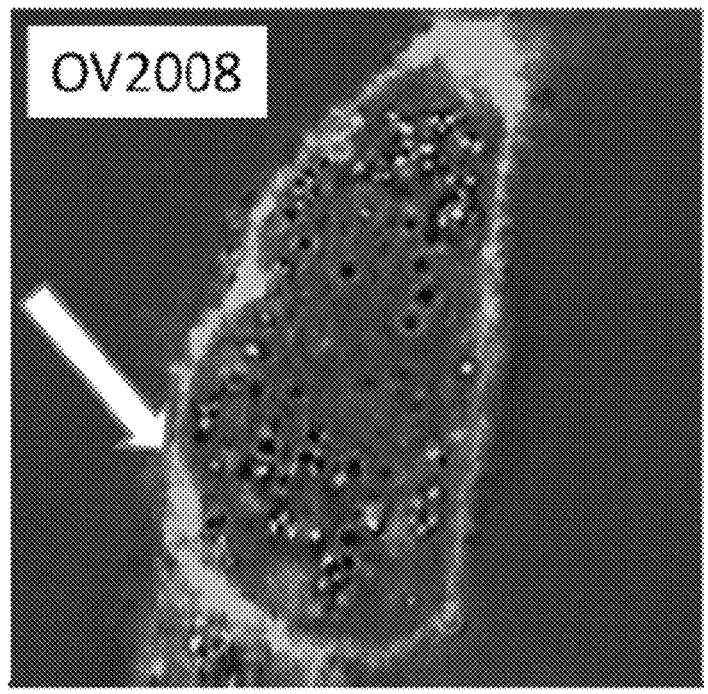
Figure 27:
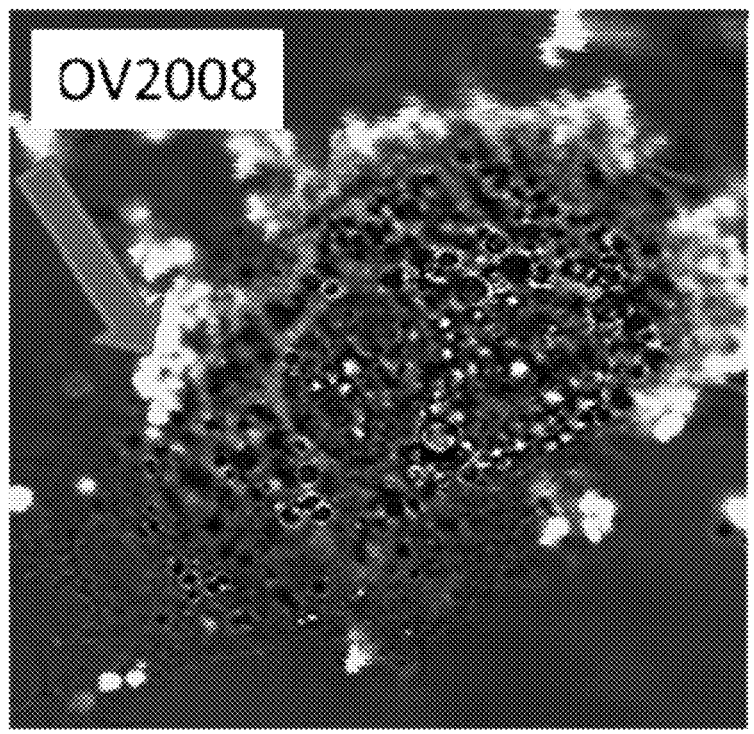

FIG. 26 is a confocal microscope image OV2008 cells exposed only to chitosan. Images were stained with wheat agglutinin/fluorescence of the cell membrane FIG. 27 is a confocal microscope image of OV2008 cells targeted by the delivery system, images were stained with wheat agglutinin/fluorescence of the cell membrane.

Figure 28:
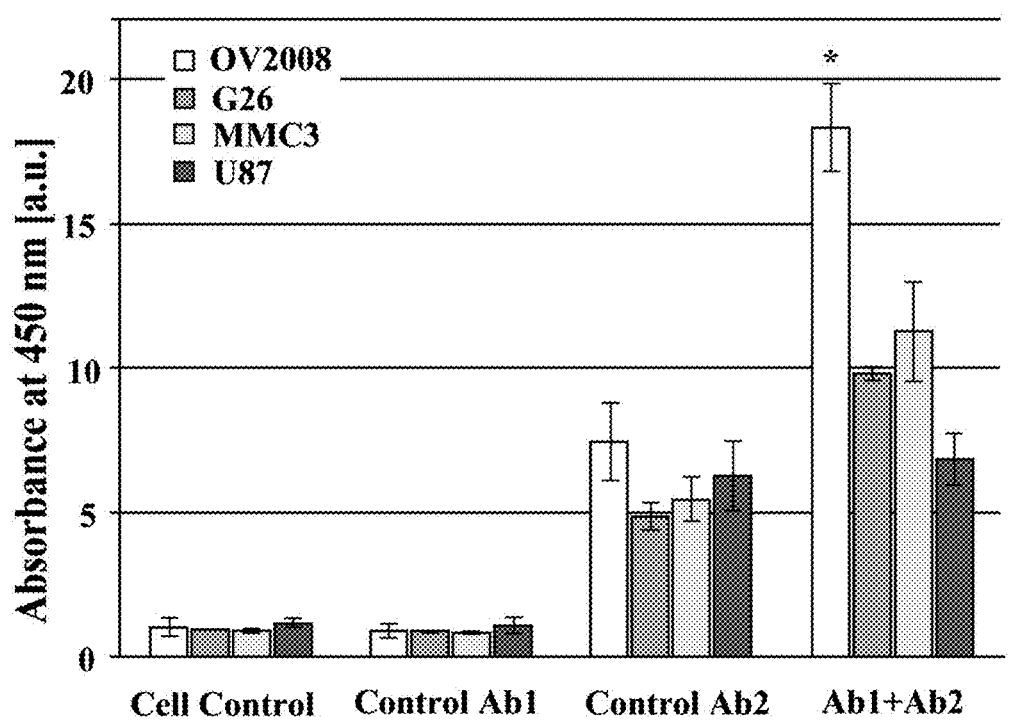

FIG. 28 is a graph showing cell-based ELISA testing for levels of MUC1 expression in cell lines.

Figure 29:
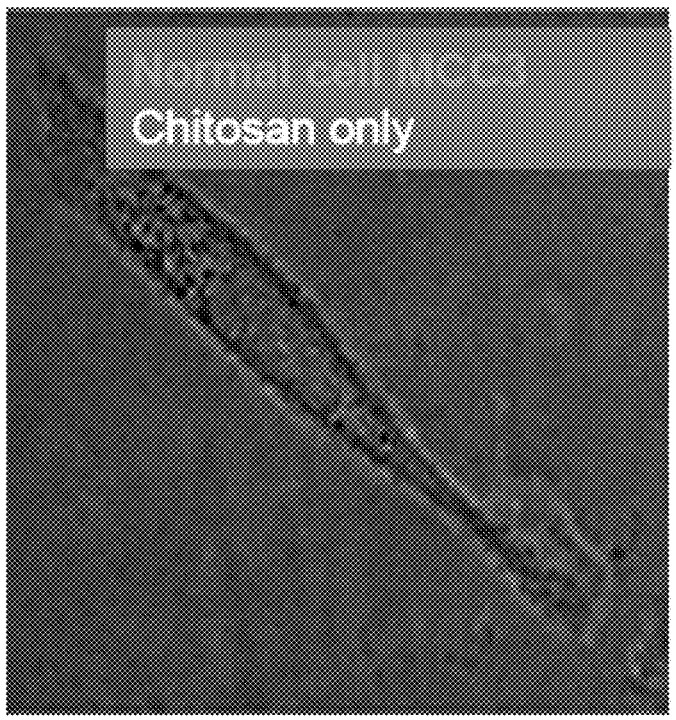

FIG. 29 is a transmission electron microscope images of MCC3 treated with chitosan for 1 hour. or OV2008 cells targeted by the delivery system. Paclitaxel was fluorescently tagged and incorporated into niosomes.

Figure 30:
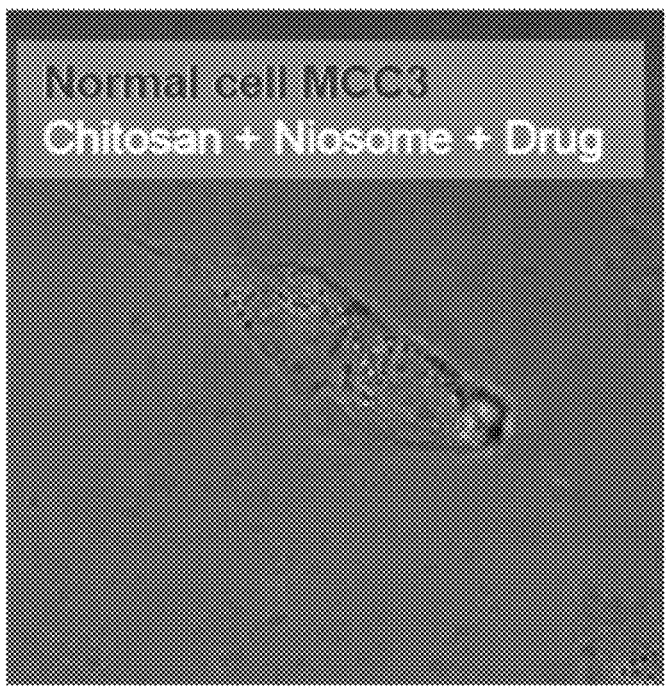

FIG. 30 is a transmission electron microscope images of MCC3 treated with the delivery system containing paclitaxel for 1 hour. Paclitaxel was fluorescently tagged with tagged with BODIPY and incorporated into niosomes.

Figure 31:
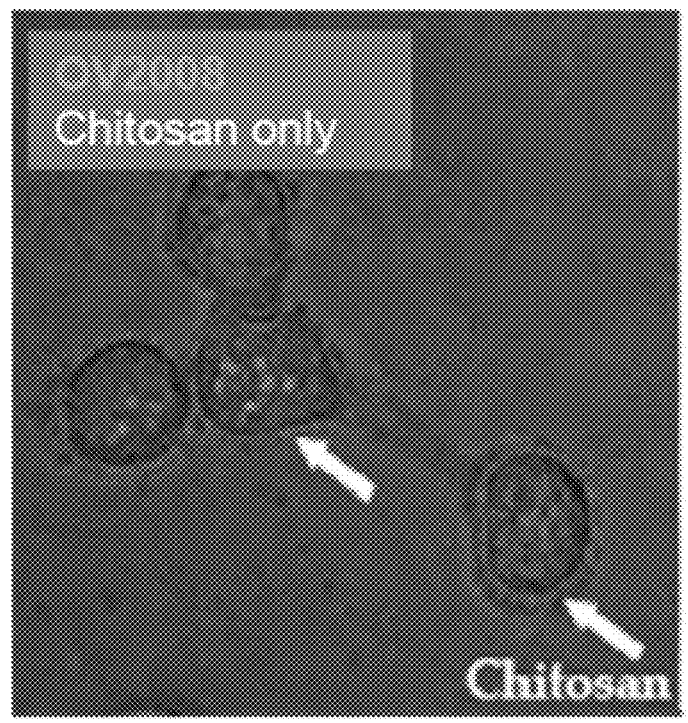

FIG. 31 is a transmission electron microscope images of OV2008 cells treated with chitosan for 1 hour. Paclitaxel was fluorescently tagged and incorporated into niosomes.

Figure 32:
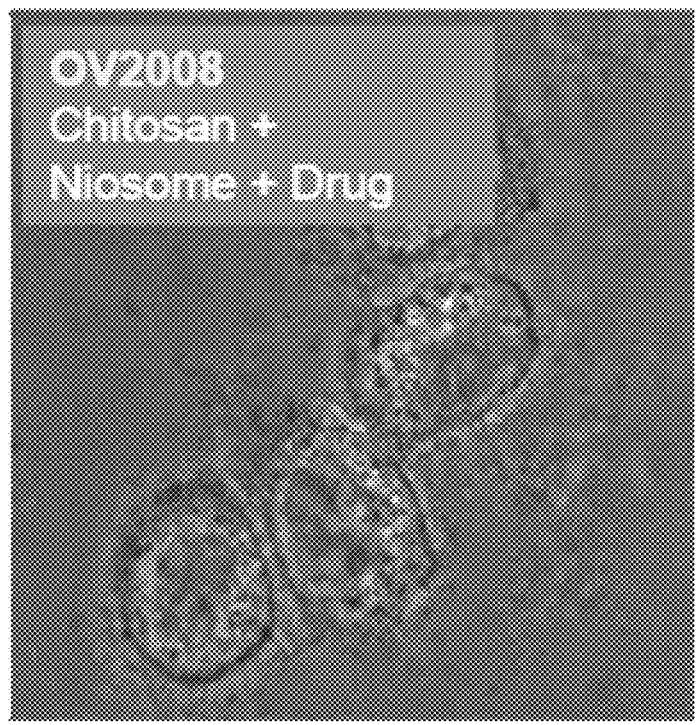
Figure 33:
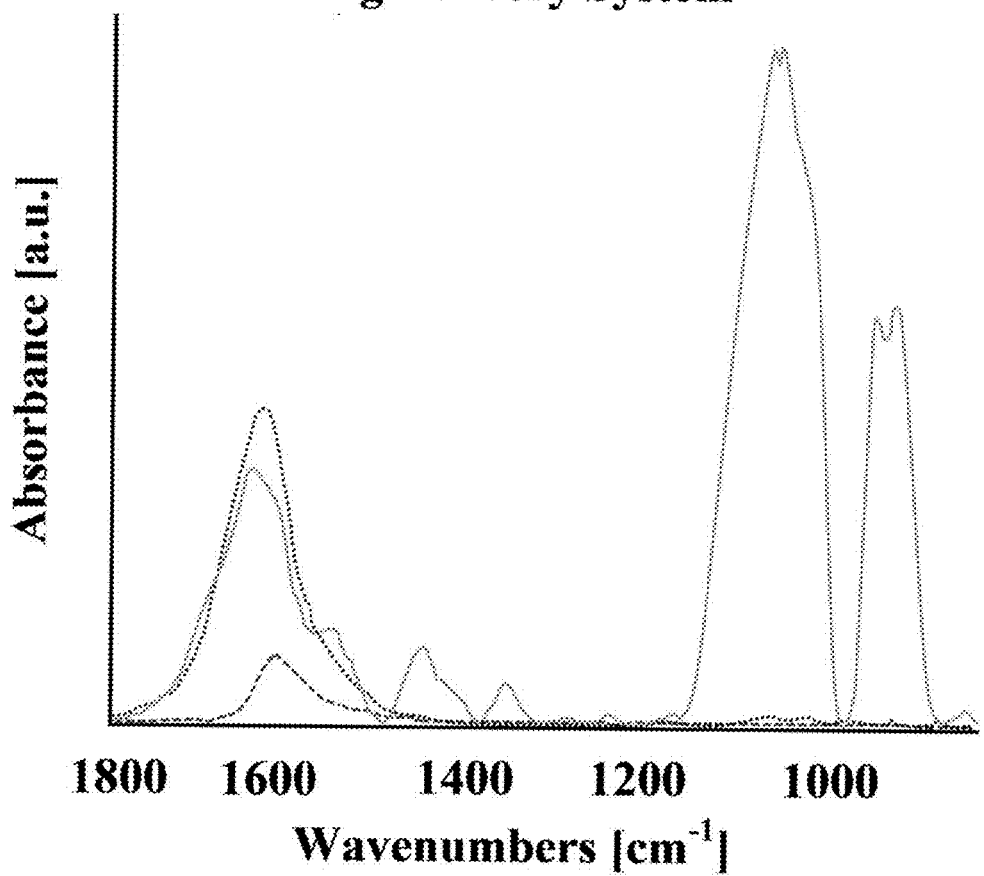

FIG. 32 is a transmission electron microscope images of OV2008 cells treated with the delivery system containing paclitaxel for 1 hour. Paclitaxel was fluorescently tagged with tagged with BODIPY and incorporated into niosomes FIG. 33 is a graph showing ATR-FTIR results of OV2008 cells exposed to paclitaxel-containing drug delivery system. OV2008 cells were examined without treatment (dark grey dashed line), treated with chitosan (grey solid line) or treated with niosomes with CTX in chitosan (black dotted line).

Figure 34:
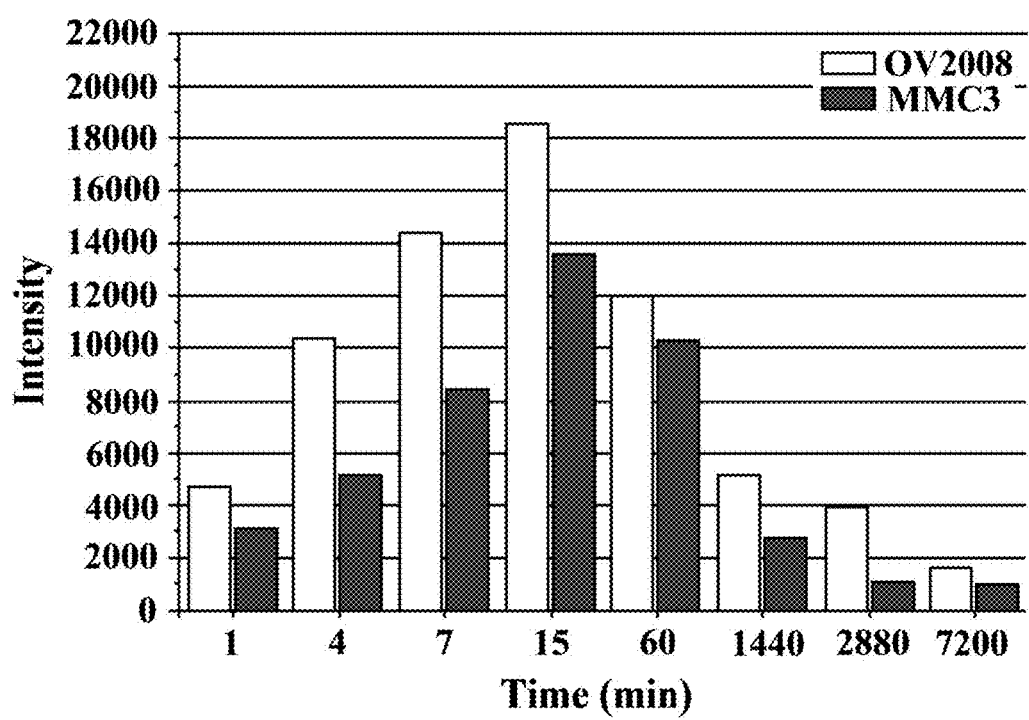

FIG. 34 is a graph showing fluorescence intensity of MCC3 or OC2008 cells after treatment with the inventive drug delivery system carrying paclitaxel.

DETAILED DESCRIPTION OF THE PREFERRED EMBODIMENT

As used herein, the singular forms "a," "an" and "the" include plural referents unless the context clearly dictates otherwise. Thus, for example, reference to "a polypeptide" includes a mixture of two or more polypeptides and the like.

As used herein, "about" means approximately or nearly and in the context of a numerical value or range set forth means±15% of the numerical.

As used herein "animal" means a multicellular, eukaryotic organism classified in the kingdom Animalia or Metazoa. The term includes, but is not limited to, mammals. Non-limiting examples include rodents, aquatic mammals, domestic animals such as dogs and cats, farm animals such as sheep, pigs, cows and horses, and humans. Wherein the terms "animal" or "mammal" or their plurals are used, it is contemplated that it also applies to any animals.

As used herein the term "patient" is understood to include an animal, especially a mammal, and more especially a human that is receiving or intended to receive treatment.

As used herein, the term "therapeutically effective amount" refers to that amount of a therapy (e.g., a chemotherapeutic agent) sufficient to result in the amelioration of cancer, or one or more symptoms thereof, prevent advancement of cancer, or cause regression of cancer.

As used herein, the term "cancer" or "cancerous" refer to or describe the physiological condition in mammals that is typically characterized by unregulated cell growth, i.e., proliferative disorders. Examples of such proliferative disorders include cancers such as carcinoma, lymphoma, blastoma, sarcoma, as well as other cancers disclosed herein. More particular examples of such cancers include glioma, colon, breast, ovarian, lung and pancreatic cancers.

Specific drug delivery to tumor cells without affecting normal cells remains a major challenge in cancer treatment. We present a localized drug delivery system with enhanced targeting ability consisting of non-ionic surfactant vesicles (niosomes) with chlorotoxin (CTX) embedded in a chitosan hydrogel. This system represents a novel approach in cancer therapy through the controlled and targeted delivery of drugs to tumor cells.

This finding demonstrates the capability of chitosan to target tumor cells expressing MUC1. Similarly, the incorporation of CTX (a 36-amino acid peptide capable of binding preferentially to tumor cells of neuroectodermal origin but not to normal cells) along with niosomes in the chitosan hydrogel is usefulas the second targeting strategy to further improve the specific delivery of drugs to tumor cells such as glioma, colon, breast, ovarian, lung and pancreatic cancers.

Example 1

Figure 1:
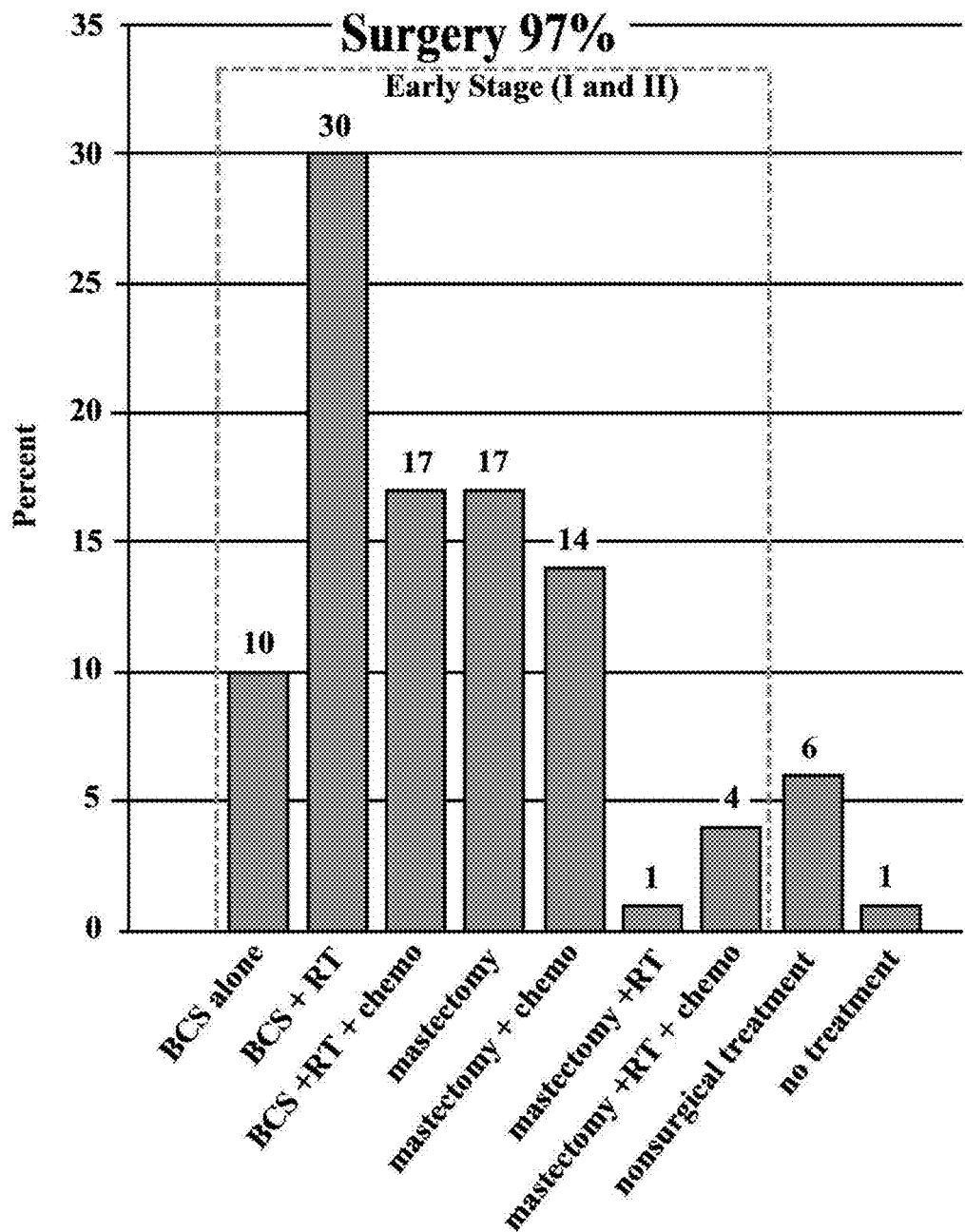
Figure 2:
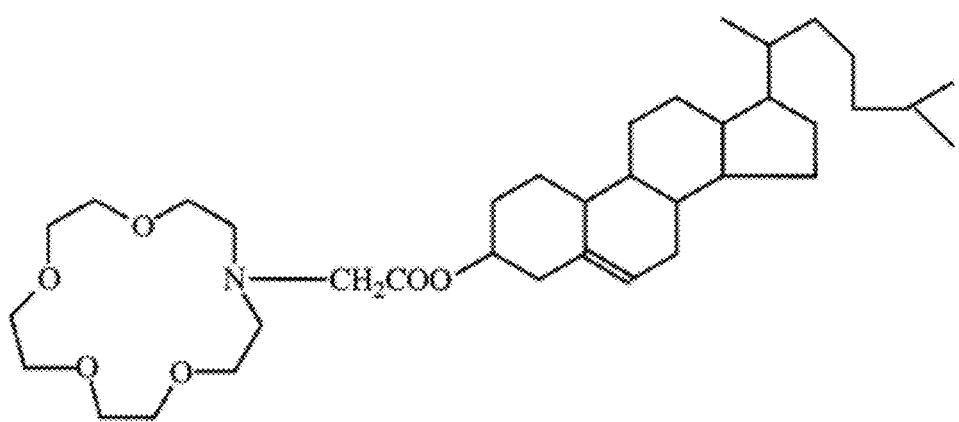
Figure 3:
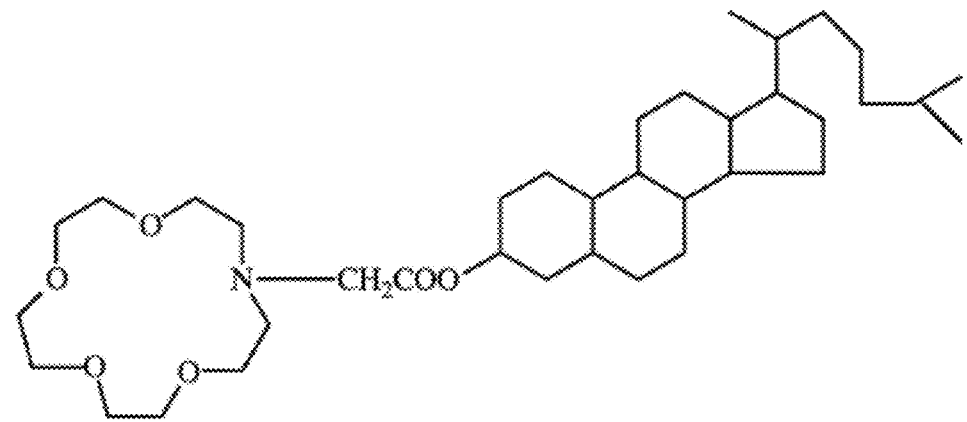

The advantage of using niosomes as opposed to liposomes is that the synthetic niosomes have shown to be more chemically stable as vesicles, they are easier to transport and store, they are less expensive, and they have been shown to increase the blood brain barrier permeability. It is composed of synthetic amphiphilic surfactants and cholesterol that make up a bilayer membrane and is able to entrap hydrophilic solutions in the aqueous core and hydrophobic solutions in the non-polar membrane. Exemplary surfactants include, without limiting the scope of the invention, crown ether amphiphiles bearing a steroidal moiety, 1,2-dialkyl glycerol polyoxyethylene ether, hexadecyl poly-5-oxyethylene ether, hexadecyl poly-5-oxyethylene ether ($C_{16}EO_5$); octadecyl poly-5-oxyethylene ether ($C_{18}EO_5$); hexadecyl diglycerol ether ($C_{16}G_2$); sorbitan monopalmitate (Span 40) and sorbitan monostearate (Span 60), Solulan™ C24 (poly-24-oxyethylene cholesteryl ether), polysorbate 20, Span detergents, Brij detergents, such as Brij-35, and polyoxyethylene. Examples of crown ethers are illustrated in FIGS. 2 and 3, and are known in the art (Echegoyen, et al., Aggregation of steroidal lariat ethers—the 1st example of non-ionic liposomes (niosomes) formed from neutral crown ether compounds. J Chem. Soc Chem Commun, 1988. 12, 836-837; Montserrat, et al., Light-induced charge injection in functional crown ether vesicles. J Am Chem Soc, 1980. 102, 5527-5529; Darwish & Uchegbu, The evaluation of crown ether based niosomes as cation containing and cationsensitive drug delivery systems. Int'l J Pharm, 1997. 159, 207-213; Uchegbu & Duncan, Niosomes containing N-(2-hydroxypropyl)methacrylamide copolymer-doxorubicin (PK1): effect of method of preparation and choice of surfactant on niosome characteristics and a preliminary study of body distribution. Int'l J Pharm, 1997. 155, 7-17). Exemplary solvents involved in noisome formation may include glycerol, oil, water, and combinations thereof.

Cholesterol provides stability to the vesicles by decreasing their permeability and enhancing solute retention (Uchegbu, & Florence, Non-ionic Surfactant Vesicles (Niosomes): Physical and Pharmaceutical Chemistry. Advances in Colloidal and Interface Science, 1995. 58: p. 1-55; Nasseri, Effect of cholesterol and temperature in the elastic properties of niosomal membranes. International Journal of Pharmaceuticals, 2005. 300: p. 95-101). More permeable membrane (cholesterol free) entrap a lower amount of the drug, decreasing the encapsulation efficiency (Uchegbu & Vyas, Non-ionic Surfactant Based Vesicles (Niosomes) in Drug Delivery. International Journal of Pharmaceutics, 1998. 172: p. 33-70; Uchegbu & Florence, Non-ionic Surfactant Vesicles (Niosomes): Physical and Pharmaceutical Chemistry. Advances in Colloidal and Interface Science, 1995. 58: p. 1-55).

In addition, negative charged molecules may be added to the bilayer-producing compounds, such as dicetyl phosphate, cetyl sulphate, phosphatidic acid, phosphatidyl serine, oleic acid, palmitic acid. Dicetyl Phosphate is used to provide electrostatic stabilization to the vesicles which prevents their aggregation (Uchegbu & Vyas, Non-ionic Surfactant Based Vesicles (Niosomes) in Drug Delivery. International Journal of Pharmaceutics, 1998. 172: p. 33-70; Manosroi, et al., Characterization of vesicles prepared with various non-ionic surfactants mixed with cholesterol. Colloids and Surfaces: Biointerfaces, 2008. 30: p. 129-138). The ability of the surfactant to form a vesicle depends on two factors, the Hydrophobic Lipophilic Balance (HLB) and the Critical Packing Parameter (CPP). The HLB is calculated using $$HLB = 20 \times Mh/M \qquad (1)$$

Where Mh is the molecular mass of the hydrophilic portion of the surfactant, and M is the molecular mass of the whole niosome, giving a result on an arbitrary scale of 0 to 20. For the surfactant sorbitan monostearate, an HLB number between 4 and 8 was found to be compatible with vesicle formation (Uchegbu & Vyas, Non-ionic Surfactant Based Vesicles (Niosomes) in Drug Delivery. Int'l J of Pharm, 1998. 172: p. 33-70).

The CPP is a dimensionless number that predicts the ability of the amphiphile to form aggregates. Israelachvili (Israelachvili, *Intermolecular and Surface Forces: With Applications to Colloidal and Biological Systems*. 1985, Orlando: Academic Press) reports that a CPP value of 0.5-1.0 predicts that the amphiphile will form a vesicle. CPP is calculated using $$CPP = v/l_c a_o \quad (2)$$

where v=hydrocarbon chain volume, $l_c$=critical hydrophobic chain length (the length above which the chain fluidity of the hydrocarbon may no longer exist), and $a_o$=area of hydrophilic head (Uchegbu & Florence, *Non-ionic Surfactant Vesicles (Niosomes): Physical and Pharmaceutical Chemistry*. Advances in Colloidal and Interface Science, 1995. 58: p. 1-55).

Figure 4:
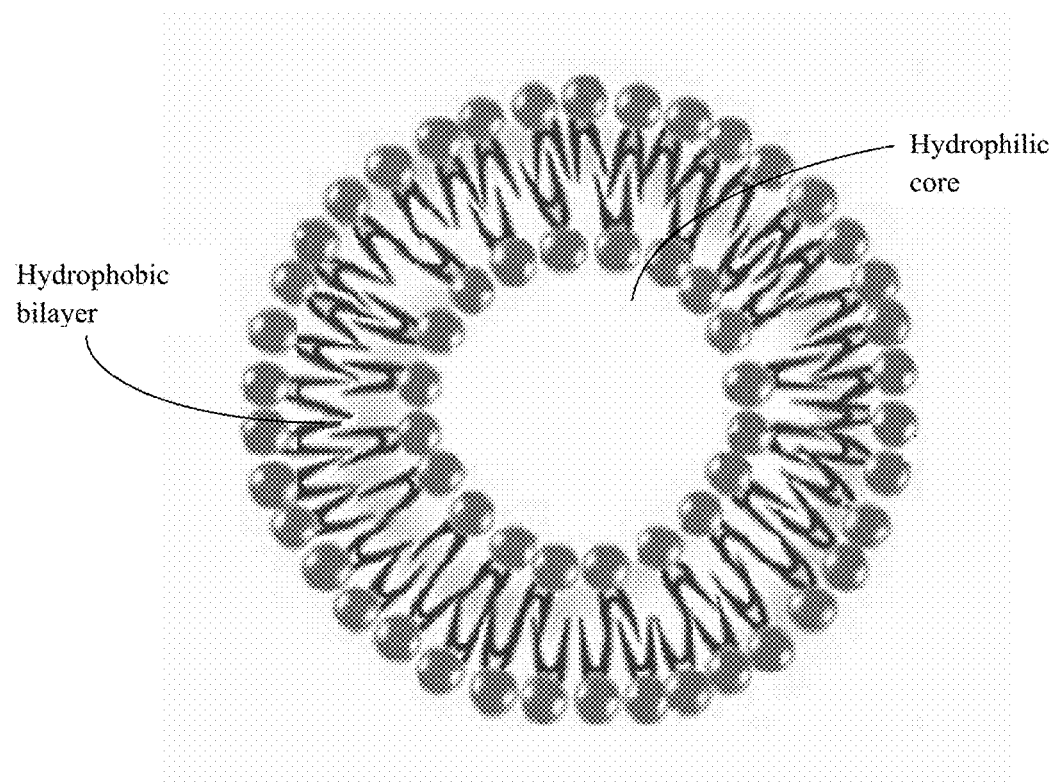
FIG. 4 is a cross-section illustration of a non-ionic surfactant vesicle/niosome, showing the membrane bilayer and internal compartment.

The niosomes were formed from the self-assembly of non-ionic amphiphiles in aqueous media resulting in closed bilayer structures (Uchegbu & Vyas, *Non-ionic Surfactant Based Vesicles (Niosomes) in Drug Delivery*. Int'l J of Pharm, 1998. 172: p. 33-70), seen in FIG. 4. The assembly into bilayers is rarely spontaneous and usually involves some input of energy such as physical agitation or heat. The result is an assembly in which hydrophobic parts of the molecule are shielded from the aqueous solvent and the hydrophilic head groups enjoy maximum contact with same (Uchegbu & Vyas, *Non-ionic Surfactant Based Vesicles (Niosomes) in Drug Delivery*. Int'l J of Pharm, 1998. 172: p. 33-70; Israelachvili, *Intermolecular and Surface Forces: With Applications to Colloidal and Biological Systems*. 1985, Orlando: Academic Press).

Niosomes were prepared by combining surfactant (Span 60), cholesterol, and, optionally, negative charged molecule (dicetyl phosphate) in the molar ratio 1:1:(0.1). 3 ml of chloroform or other solvent was added to it and the solution transferred to a 50 mL round bottom flask attached to a rotary evaporator (Buchï). The solution was agitated in a 60° C. bath until all the solids dissolved. Any reduction in the volume of solution was compensated for by adding an equal amount of solvent. $N_2$ gas was passed through the flask while rotating till the chloroform evaporates, forming uniform thin layer on the flask. $N_2$ gas flow was continued for at least 10 min after all of the chloroform has evaporated.

The flask is left upturned in a fume hood to dry for at least 8 hrs, to overnight, to remove any excess chloroform. The thin film was then hydrated by adding 0.01 M PBS, 5.0 mM 5(6)-carboxyfluorescein solution and placed in the rotary evaporator in a 60° C. water bath for 1-2 hours. However, a hydrophilic drug may be used in place of the 5(6)-carboxyfluorescein solution. It is very important to prepare niosomes at temperature above the gel-liquid transition temperature of the non-ionic surfactants. The phase transition temperature of Span 60 is about 50° C. Therefore, all the preparation steps were carried out at 60° C. The flask was placed in a bath is maintained at 60° C. for 1 hr or until all the film dissolved. The flask was taken out of the bath and left to cool.

Size reduction was performed using a Mini-Extruder (Avanti Polar Lipids), through polycarbonate membrane filters (Nucleopore) of 800, 400, and 80 nm at 60° C. Niosome dispersion was taken in one syringe and passed through the extruder into the other syringe. This process was repeated at least 12 times. The un-entrapped solute from the niosomes was separated by ultracentrifuge (Beckman, XL-100, Fullerton, Calif., USA) at 60,000 rpm for 1 h at room temperature. The dye loaded niosomes in the precipitate were redispersed in PBS and kept in 4° C. for further studies.

The size distribution of niosomes was found to be function of the encapsulated dye, provided by:

$$average \text{ size (nm)} = 749.25(\text{nm}) + 23.16\left(\frac{\text{nm}}{mM}\right) \times [Dye(mM)]$$

Figure 5:
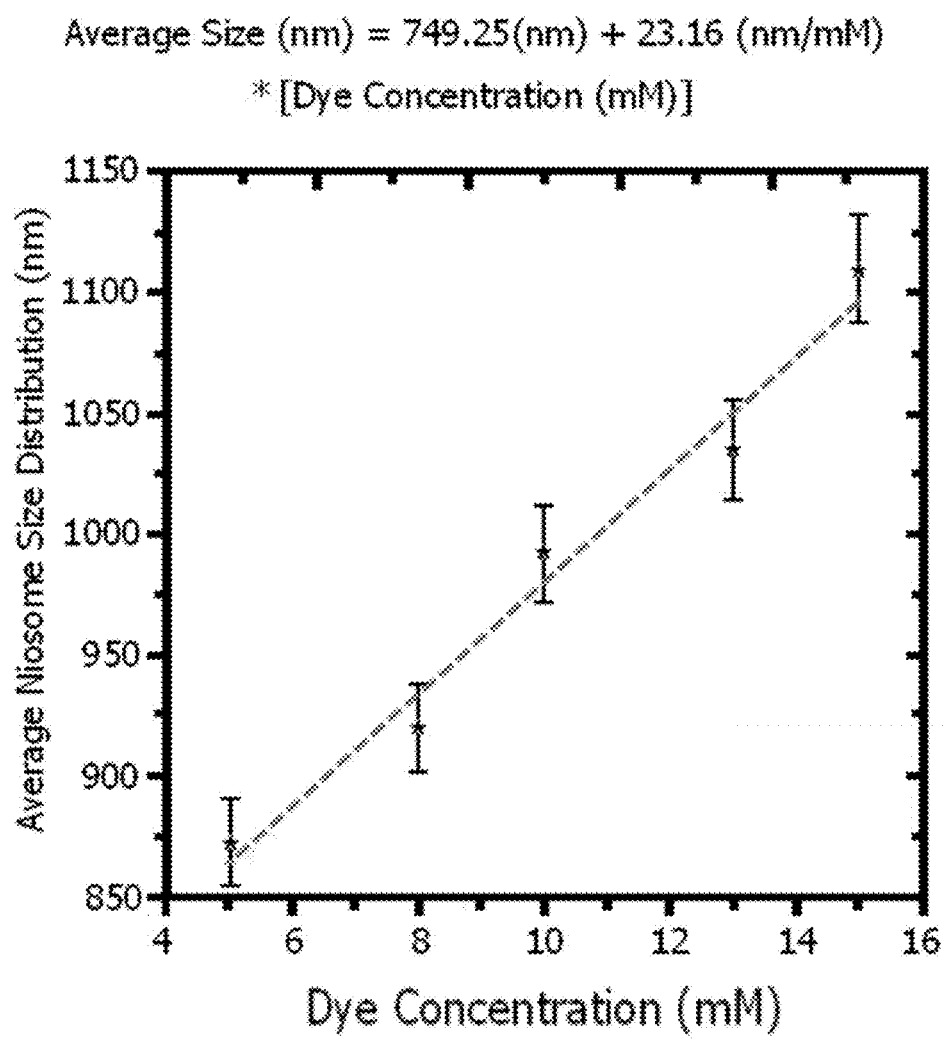
FIG. 5 is a graph showing the size distribution of niosomes as a function of the encapsulated dye. The linear trend of the plot assists in predicting the size of niosomes for a given dye concentration.

The linear trend of the plot assists in predicting the size of niosomes for a given dye or drug concentration. A range of dye concentrations from 5 millimolar (mM) to 15 millimolar (mM) were tested for niosome size and release rate, as seen in FIG. 5.

Figure 6:
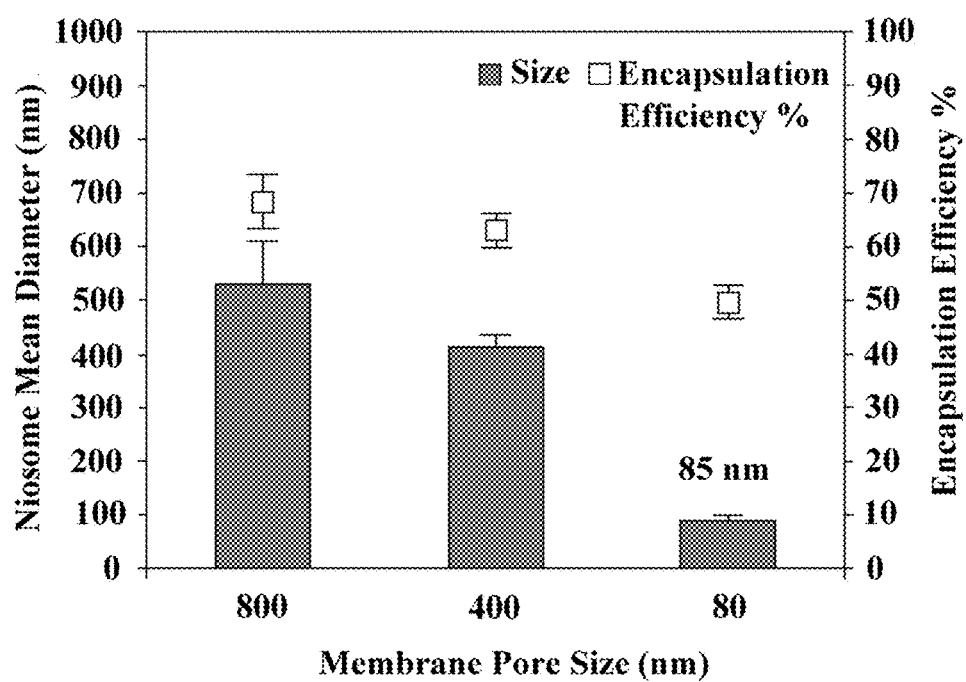
FIG. 6 is a graph showing drug encapsulation efficiency related to niosome size.

Furthermore, the diameter of the niosome, i.e. the size, controls the encapsulation efficiency of the niosome. Thus, larger niosomes are able to encapsulate more drug increasing the encapsulation efficiency, as seen in FIG. 6.

Niosome stability and drug release were tested. Niosome release drugs based on either concentration gradients or due to increased osmotic pressure. Difference in the concentration of ions between niosomes and deionized water lead to an increase in the osmotic pressure resulting in an uncontrolled rupture of the niosomes, and hence a higher concentrations and percentages of drug are released as compared to PBS, depicted in FIGS. 7 and 8. Since the microenvironment surrounding tumors differs from physiological conditions, with less ions and lower pH, the microenvironment surrounding tumors will result in greater levels of chemotherapeutic at the tumor site.

Example 2

Surfactant Span-60, cholesterol and dicetyl phosphate in a molar ratio of 1:1:0.1 were dissolved in 3 ml of chloroform. Paclitaxel was added to this solution. Thin film was made using the same technique mentioned in Example 1. The dried thin film was hydrated by adding 4 ml of 0.01 M PBS and placed in the rotary evaporator in a 60° C. water bath for 1-2 hours.

The same methodologies for size reduction, separation of the un-entrapped solute, and resuspension of vesicles described in Example 1 were applied to niosomes with paclitaxel. For cell-free and in-vitro release rate studies the initial concentration of 5 mM was used for paclitaxel. Stability analysis showed attaching CTX to the niosome reduced paclitaxel release from the niosomes, regardless of pH differences in the release media.

To generate niosomes containing two drugs, a hydrophobic and hydrophilic drug, the thin film is prepared by combining surfactant, cholesterol, a hydrophobic drug, and, optionally, negative charged molecules. As an example only, niosomes were created with Span 60, cholesterol, dicetyl phosphate and the Paclitaxel. Hydration is performed using a hydrophilic drug, such as Carboplatin. During the hydration process the hydrophobic parts of the system are shielded away from the hydrating solution whereas the hydrophilic parts share absolute contact with the same. Because the hydrophobic drugs are packaged in different regions of the niosome than the hydrophilic drugs, the drugs do not come in contact at any point until the niosomes are delivered to the target site. Therefore, any kind of hydrophobic and hydrophilic drug can be used for encapsulation. The combination hydrophobic-hydrophilic-drug niosome can be employed to include a wide variety of hydrophobic and hydrophilic drugs, such as Triciribine and Carboplatin.

All the mixture of drugs that have been used in 'combination chemotherapy' can be used for encapsulation in the drug delivery system. In a first method to produce niosomes utilizing thin films described above, the surfactant Span 60, cholesterol and dicetyl phosphate, hydrating them with the dye, constricting their size by extrusion and removal of the free dye by ultracentrifugation. In a second method all the steps till the hydration were the same after which they were sonicated for 15 min. The free dye was removed using Gel Exclusion Chromatography. The niosomes prepared by the two methods were compared for stability, encapsulation efficiency and dye release rate. The size distribution of the niosomes was determined by Dynamic Light Scattering and Transmission Electron Microscopy.

Example 3

9 ml of 2.78% (w/v) chitosan and 3 ml of 65% (w/v)β-glycerophosphate solutions were prepared in aqueous solution of HCl (0.1 M) and deionized water respectively. Both solutions were kept in 4° C. for 1 hour prior to crosslinking. Stirring continuously the cooled β-glycerophosphate solution was added drop wise to the chitosan solution. After adding the last drop, the final solution was stirred for additional 10 minutes.

Chitosan, an amino-polysaccharide obtained by alkaline deacetylation of chitin, a natural component of shrimp or crab shells, is a biocompatible and biodegradable, pH-dependent, cationic polymer (Chenite, et al., *Novel injectable solutions of chitosan from biodegradable gels in situ*. Biomaterials, 2000: p. 2155-2161). It is a copolymer of glucosamine and N-acetyl glucosamine and is known to be digestible by lysozyme according to the amount of N-acetyl groups and their distribution in the backbone (Ruel-Gariepy, et al., *Characterization of Thermosensitive Chitosan Gels for the Sustained Delivery of Drugs*. International Journal of Pharmaceutics, 2000. 203: p. 89-98), and it is both abundant and has a low cost making it both feasible and economical. It was found that the thermo-sensitive chitosan hydrogel functioned particularly well when the degree of deacetylation is between 75-85%.

Three different molecular weights of chitosan were used to embed the niosomes encapsulated with the dye. The ranges of the molecular weights are as shown in Table 1.

TABLE 1

Range of chitosan molecular weights used to form the hydrogel.

| Low Molecular Weight (LMW) | Medium Molecular Weight (MMW) | Practical Crude Grade (PG) |
|---|---|---|
| 50000-190000 Da | 190000-310000 Da | 190000-375000 Da |

Medium molecular weight chitosan was found to have the finest controlled release. Hence, further experiments were conducted using this grade of chitosan.

Chitosan stability was determined using chitosan with a degree of deacetylation of 85%. Hydrogels were formed using β-glycerophosphate, and split into two, with a piece of the chitosan hydrogel placed into 1×PBS or 0.2 mg/ml lysozyme in 1×PBS. As seen in FIG. 9, lysozyme degraded 74% of the hydrogel in 49 days, whereas the gel in PBS showed degradation of about 30%. Since lysozyme circulates throughout the body, chitosan will be degraded over time, releasing niosomes containing drug.

In some embodiments of the invention, the chitosan is made to respond to external stimuli such as temperature, pH and ionic strength (Molinaro, et al. *Biocompatibility of thermosensitive chitosan-based hydrogels: an in vivo experimental approach to injectable biomaterials*. Biomaterial, 2002. 23: p. 2717-2722), by the addition of certain polyols (Ta, et al., *Injectable chitosan hydrogels for localized cancer therapy*. J Controlled Release, 2008. 126: p. 205-216). An exemplary compound is β-glycerophosphate, which neutralizes the chitosan solution and renders the chitosan temperature-sensitive. Such systems are liquid at room temperature and gel once the solution reaches body temperature (37° C.). This property can be especially useful in the present system, allowing the composition to be injectable and avoiding the cost of surgeries as in the case of implants. Further, the pH needed to induce gellation is varied depending on the amount of cross-linker added to it, as seen below.

β-glycerophosphate plays three essential roles; it increases the gellation pH to the physiological range of 7.0-7.4; it prevents immediate precipitation or gelation; and it allows for controlled hydrogel formation when an increase in temperature is imposed (Chenite, et al., *Novel injectable solutions of chitosan from biodegradable gels in situ*. Biomaterials, 2000: p. 2155-2161; Ruel-Gariepy, et al., *Characterization of Thermosensitive Chitosan Gels for the Sustained Delivery of Drugs*. International Journal of Pharmaceutics, 2000. 203: p. 89-98; Chenite, et al., *Rheological characterization of thermogelling chitosa/glycerophosphate solutions*. Carbohydrate Polymers, 2001. 46: p. 39-47). A range of crosslink densities were tested for their gelling and dye release rate. Table 2 shows the various ratios of the cross-linker β-Glycerophosphate and Chitosan and their corresponding pH. Gelling of the chitosan system occurred only in the ratio range (3.5):1 to (4.5):1. This corresponded to a pH range from 6.9 to 7.9 which convey the fact that the drug system is thermo-sensitive only around the physiological pH range.

TABLE 2

Crosslinking properties for differing ratios of β-Glycerophosphate and Chitosan.

| | β-GP:Chitosan | | | | | | |
|---|---|---|---|---|---|---|---|
| | (3.0):1 | (3.25):1 | (3.5):1 | (4.0):1 | (4.5):1 | (4.75):1 | (5.0):1 |
| pH | 6.6 | 6.7 | 6.9 | 7.4 | 7.9 | 8.1 | 8.3 |

The ratio (4.0):1 gave the finest controlled release as its pH corresponded to that of the niosomes which provided greater stability to the niosomes and hence lower release. Further experiments were conducted using this crosslink density ratio.

Chitosan is typically not soluble in water, but its solutions can be obtained in acidic aqueous media which protonate chitosan amino groups, rendering the polymer positively charged and thereby overcoming associative forces between chains (Chenite, et al., *Rheological characterization of thermogelling chitosan/glycerophosphate solutions*. Carbohydrate Polymers, 2001. 46: p. 39-47). Factors which determine the ease of gelling of the chitosan is its degree of deacetylation and the molecular weight (Ruel-Gariepy, et al., *Thermosensitive Chitosan-Based Hydrogel Containing Lipsomes for the Delivery of Hydrophilic Molecules*. J of Controlled Release, 2002. 82: p. 373-383; Ruel-Gariepy, et al., *A Thermosensitive Chitosan-Based Hydrogel for the*

*Local Delivery of Paclitaxel.* Eur J of Pharm and Biopharm, 2004. 57(53-63); Ruel-Gariepy & Leroux, *In Situ-Forming Hydrogels—Review of Temperature-Sensitive Systems.* Eur J of Pharm and Biopharm, 2004. 58: p. 409-426; Cho, et al., *Physical Gelation of Chitosan in the Presence of β-Glycerophosphate*: The Effect of Temperature. Biomacromolecules 2005. 6: p. 3267-3275; Kempe, et al., *Characterization of Thermosensitive chitosan based hydrogels by rheology and electron paramagnetic resonance spectroscopy.* Eur J of Pharm and Biopharm, 2008. 68; p. 26-33; Cho & Heuzey, *Dynamic scaling for gelation of a thermosensitive chitosan-β glycerophosphate hydrogel.* Colloid Polymer Science, 2008. 286: p. 427-434; Zhou, et al., *Effect of molecular weight and degree of deacetylation on the preparation and characteristics of chitosan thermosensitive hydrogel as a delivery system.* Carbohydrate Polymers, 2008. 73: p. 265-273; Peppas, *Polymers in controlled drug delivery.* Med Plastics and Biomat Magazine. 1997; Parthasarathi, et al., *Niosome Encapsulated of Vincristine Sulfate: Improved Anticancer Activity with Reduced Toxicity in Mice.* J of Drug Target, 1994. 2(2): p. 173-183).

Further, the amount of niosomes loaded into the chitosan network was also found to have an effect on the rate of dye released into the surroundings. Niosome: Chitosan ratios ranging from (0.15):1 to (0.45):1 were previously investigated for their dye release, and an optimum ratio of (0.35):1 which resulted in the finest controlled release. This in turn results in a loosely packed structure and hence a higher release rate. This result is particularly important when a high dose is required for a short period of time or a low dose for an extended period. Depending on the drug dosage and time period the system can be fined tuned to suit the requirement at hand.

The use of chitosan with niosomes improves the stability of the niosome delivery system. Placing niosomes in salt-free water results in osmotic rupturing of the niosomal membrane in a time-dependent manner with about 65% ruptured by 48 hours and over 90% of niosomes ruptured within 120 hours, as seen in FIG. 10. By comparison, chitosan protected the niosomes from rupture, with less than 40% ruptured by 48 hours and around 40% ruptured within 120 hours. Chitosan retained niosomal stability through 240 hours, with only about 45% of dye released. Additional testing showed chitosan prevented rupture with only a 20% release of dye through to 144 hours, as seen in FIG. 11. Using paclitaxel as a model drug, the chitosan protected the niosomes from the environment, as salt-free water and PBS environments showed low amounts of drug release, up to about 37% by 12 days of exposure, as seen in FIG. 12.

Other useful hydrogels may be formed using a polymer hydrogel that is adapted to respond to temperature or solution pH, such as poly(vinyl methyl ether) (PVME), poly(2-(2-methoxyethoxy)ethyl methacrylate) (PMEO2MA), acryloyl-L-proline methyl ester (A-ProOMe), poly(N, N-diethylacrylamide), poly(N-vinylcaprolactam) (PVCL), poly-(ethylene oxide) and polypropylene oxide) block copolymer, poly(acrylamide), or poly-NIPAAm (N-isopropylacrylamide), which is described by Hoffman, et al. (U.S. Pat. No. 4,912,032); Chen, et al. (U.S. Pat. No. 6,486,213); Bae, et al. (U.S. Pat. No. 5,262,055); West, et al. (U.S. Pat. No. 6,428,811). A non-limiting example of such a poly-NIPAAm hydrogel is formed from 20% (w/v) recrystallized NIPAAm in deionized water, and methylene-bis-acrylamide (MBAAm) at a 1:750 molar ratio to NIPAAm. Ammonium persulfate (APS) and tetramethylethylenediamine (TEMED) initiated a redox reaction to polymerize the hydrogel. Previous work with these systems has shown a temperature-dependent release of drug from the system, as seen in Hoffman, et al. (U.S. Pat. No. 4,912,032).

Release rates of drug in the niosome-chitosan delivery system were analyzed for different concentrations of chitosan, as seen in Table 3. Samples of niosomes with paclitaxel embedded in chitosan hydrogel were placed into 30 ml of PBS (pH=7.4 or 6.30) containing 0.1% (v/v) Tween 80 at 37° C. At specific time points, the release medium was collected and replaced with equal amount of fresh medium at 37° C. The amount of paclitaxel released into the medium was determined using Shimadzu HPLC system. The mobile phase of the HPLC consisted of water and acetonitrile (60:40 v/v) at a flow rate of 1.0 mL/min, an injection volume is 20 ml, and detection wavelength is 227 nm.

TABLE 3

Chitosan hydrogel formulations with different amounts of crosslinker (β-glycerophosphate).

| sample | β-glycerophosphate % (w/v) | Chitosan % (w/v) |
|---|---|---|
| L-Ch Nio | 10 | 1.5 |
| M-Ch Nio | 12 | 1.5 |
| H-Ch Nio | 15 | 1.5 |

The inclusion of niosomes into low concentration chitosan hydrogels showed a predicted time-dependent release of paclitaxel, which was found to increase at a slightly basic pH, compared to a slightly acidic pH, as seen in FIG. 13. Swelling of the chitosan hydrogels occurred in PBS with pH of 6.3, due to $NH_2$ groups in chitosan becoming protonated below a pH of 6.5 and repulsion between $NH_3^+$ groups leading to swelling of the hydrogel. By comparison, no swelling behavior was observed for chitosan hydrogels incubated in PBS with pH of 7.4. Medium concentrations of chitosan mirrored the low concentration results, as seen in FIG. 14, whereas high concentration chitosan hydrogels reduced both basic and acidic release of paclitaxel, as seen in FIG. 15. As expected, due to the hydrogel swelling properties, release rate for all chitosan formulations was slower in PBS with pH of 6.3 than PBS with pH of 7.4.

The release data were further analyzed by the Korsmeyer and Peppas Model, which provides:

$$Q = (M_t/M) = k \times t^n$$

where:

Q: fractional drug release into the dissolution medium at time t

Mt: amount of drug released at time t

M: total amount of drug k: constant related to structural and geometric characteristics of the drug delivery system n: diffusional exponent indicative of the mechanism of drug release $n<0.5$ quasi-Fickian diffusion;

$n=0.5$ Fickian diffusion;

$0.5<n<1$, anomalous transport;

$n=1$, non-Fickian;

Case-II transport (zero-order release)

$n>1$, non-Fickian special case-II transport.

The results of the model are shown in Table 4.

TABLE 4

Korsmeyer-Pappas analysis of the release kinestics.

| | Korsmeyer-Pappas model | | | Drug release |
|---|---|---|---|---|
| sample | k | n | $R^2$ | mechanism |
| L-Ch Nio9- PBS, pH 6.3 | 0.517968 | 0.573125 | 0.959614 | anomalous transport |

TABLE 4-continued

Korsmeyer-Pappas analysis of the release kinetics.

| sample | Korsmeyer-Pappas model | | | Drug release mechanism |
| --- | --- | --- | --- | --- |
| | k | n | $R^2$ | |
| L-Ch Nio9- PBS, pH 7.4 | 0.790746 | 0.540332 | 0.955353 | anomalous transport |
| M-Ch Nio9- PBS, pH 6.3 | 0.548961 | 0.558536 | 0.937217 | anomalous transport |
| H-Ch Nio9- PBS, pH 6.3 | 0.222781 | 0.68384 | 0.990586 | anomalous transport |
| H-Ch Nio9- PBS, pH 7.4 | 0.222781 | 0.736174 | 0.914562 | anomalous transport |

Niosomes contain dicetyl phosphate (DCP) which is a negative charge inducer, and are therefore negatively charged with zeta potentials between −41.3 and −77.3 mV. Due to the positive charges on chitosan, as discussed above, the negative charge on niosomes interact with positively charged $NH_2$ groups in chitosan hydrogel when incubated in PBS with low pH (6.3). Thus, it is speculated that the slower release rates at pH 6.3 are likely due to interactions between the positively charged amines of chitosan at the lower pH.

Example 4

Previously prepared and stored niosome suspensions in 4° C. were left to equilibrate at room temperature and mixed with chlorotoxin 0.5 mg/ml in PBS. The mixture was added into chitosan and β-glycerophosphate solution and mixed by manual stirring to ensure complete and uniform distribution. The final mixture was then heated to 37° C. (body temperature) to facilitate cross-linking Niosome/chlorotoxin to chitosan/β-glycerophosphate volume ratio of 0.35:1. Cross-linked chitosan is a transparent solution at room temperature and transforms into a soft gel at 37° C. The size of the mesh in this network is controllable based on crosslinking, etc, enhancing testing molecules release. By embedding niosomes in a chitosan network, release rates and dosages are finely tuned. Dye release from niosomes alone versus niosomes in chitosan showed that the release time for the dye inside niosomes embedded in chitosan was greatly extended.

Tests incorporating CTX with niosomes and chitosan were conducted in cell-free system. Transmission Electron Microscopy (TEM) was used to morphology assess of CTX and niosomes as well as chitosan hydrogel embedded with niosomes and CTX. The relative sizes of niosomes and chlorotoxin protein are shown in FIGS. 16 and 17. The addition of CTX to niosomes resulted in the chlorotixin associating with the exterior surface of the niosomal membrane, as seen in FIG. 18. Moreover, numerous CTX molecules associate, surrounding the niosome. The inclusion of the niosome-CTX molecules into chitosan did not disrupt the CTX association with the niosomes, as seen in FIG. 19.

In vitro release studies were performed to examine the effect of CTX release rates and release kinetics using High Performance Liquid Chromatography (HPLC) and Attenuated Total Reflectance-Fourier Transform Infra-Red (ATR-FTIR) spectroscopy. The niosomes were incorporated into chitosan, with or without CTX. Release within 24 hours mostly relates to the dye release from niosomes when they are at the edge of the chitosan network. Therefore, both systems exhibit similar release rates, as seen in FIG. 20. Embedding CTX along with the niosomes does not disturb the controlled release from the chitosan network. The slower release rates of the CTX-associated niosomes after 24 hours indicate that niosomes embedded after the edge of the chitosan network have CTX providing them with extra stability in chitosan hydrogel, resulting in extended release rates. Further, attaching CTX to the niosomal surface resulted in longer retention of CTX-coated niosomes in the chitosan hydrogel, as seen by the reduced release percentages seen in FIG. 21.

These results compare favorably to bare niosomes, or even non-CTX niosomes embedded in chitosan, seen in FIG. 22. Interestingly, embedding CTX concurrently with niosomes, i.e. not associating the two components, did not have any effect on the release rates. Results were compared to an established TNDS delivery system to better determine CTX specific chemical binding sites along with the sites already determined to be specific for MUC1.

Based on these findings, the CTX-associated niosomal-chitosan drug delivery system described improves tumor cell uptake of drugs due to the enhanced tumor targeting and its controlled, sustained and localized drug delivery to cancer cells.

Example 5

The interactions between chlorotoxin and nonionic surfactant vesicles (niosomes) were analyzed using Attenuated Total Reflection Fourier Transform Infra-Red (ATR-FTIR) Spectroscopy. The FTIR spectra were obtained using a Nicolet 6700 spectrometer (Thermo Fisher Scientific, US). 100 μl of samples were introduced onto a 45° ZnSe flat crystal (Thermo Scientific, US) and allowed to air dry for 1 hour. In order to remove any excess water, the formed films were exposed to an ultrapure nitrogen flux before collecting the spectra. The spectra in the 4000-400 $cm^{-1}$ region were collected using 300 scans at a spectral resolution of 4 $cm^{-1}$.

FIG. 23 shows comparative spectra including Niosomes alone (Niosome), Chlorotoxin alone (CTX), and a combination of Chlorotoxin and Niosomes (CTX+Niosome). The characteristic peaks of niosome at 2917 and 2849 $cm^{-1}$ correspond to stretching vibrations of $CH_2$ and $CH_3$ of cholesterol present in the niosome structure. The peaks at 1736 and 1466 $cm^{-1}$ represent C=O stretching and $CH_2$ bending vibrations in the niosome spectrum. The characteristic peaks of CTX at 1643 and 1536 $cm^{-1}$ correspond to C=O stretch in Amide I and NH bending and CN stretch in Amide II respectively.

Three remarkable spectral shifts can be observed between CTX and CTX+Niosome: 1) the characteristic Amide II peak at 1536 cm-1 due to NH bending and CN stretch in CTX shifts to 1548 $cm^{-1}$ in CTX+Niosome, 2) the Amide I peak due to the C=O stretch at 1643 $cm^{-1}$ in CTX shifts to 1657 $cm^{-1}$ in CTX+Niosome, 3) the peak at 3286 $cm^{-1}$ due to the OH stretch in CTX shifts to 3436 cm-1 in CTX+Niosome. These shifts indicate the interactions of CTX with niosomes due to the hydrogen bonding.

Example 6

The studies in cell-free system showed that the release rates could be finely controlled depending on the specific design of the CTX-niosome-chitosan system e.g., ratio of niosomes to chitosan and amount of crosslinker for the chitosan network. It was expected that CTX in the CTX-niosome-chitosan system was useful to enhance uptake of chemotherapeutics such as paclitaxel, when compared to the noisome-chitosan delivery system without CTX.

The chitosan hydrogel was tested against two cell lines; an ovarian cancer line, OV2008, and a control (noncancerous) ovarian cell, MCC3. CTX-associated niosomes embedded in chitosan was tested for specific binding to cancer cells. The CTX-niosome-chitosan system was applied to cell cultures, and stained with fluorescently-labeled wheat agglutinin. The chitosan hydrogel showed no significant binding to the cell membrane of control cells (MCC3), as seen in FIGS. 24 and 25. Images showed chitosan specifically bound to and surrounded showed OV2008 cells after 1 hour of exposure, resulting in a granular staining pattern, as seen in FIGS. 26 and 27.

The expression level of MUC1 in different cell lines was quantitatively evaluated using Cell based Enzyme Linked Immunosorbent Assay (Cell-ELISA) to better understand the mechanism involved in interactions between chitosan and specific tumor cells. Cell-ELISA data revealed high expression level of MUC1 in ovarian epithelial carcinoma cell line (OV2008) and a moderate expression level in normal ovarian epithelial cell line (MCC3) implicating higher affinity of chitosan for OV2008 than MCC3 cell lines. In fact, OV2008 cells showed a 1.5-fold upregulation of MUC1 compared to normal (MCC3) cells, as seen in FIG. 28. It was found that there is a specific interaction between chitosan and Mucin1 (MUC1) receptors over expressed in epithelial ovarian carcinoma resulting in higher chitosan accumulation on the cancer cell surface than on normal ovarian epithelial cells.

The expression level of MUC1 in different cell lines was quantitatively evaluated using Cell based Enzyme Linked Immunosorbent Assay (Cell-ELISA) to better understand the mechanism involved in interactions between chitosan and specific tumor cells. Cell-ELISA data revealed high expression level of MUC1 in ovarian epithelial carcinoma cell line (OV2008) and a moderate expression level in normal ovarian epithelial cell line (MCC3). Specific drug delivery to tumor cells without affecting normal cells remains a major challenge in cancer treatment.

Analysis showed this preferential delivery of the CTX-niosome-chitosan system was due to chitosan interactions with mucin 1 (MUC1). A great advantage of the CTX-niosome-chitosan delivery system is that it has an intrinsic affinity to the surface of tumor cells, as the delivery system's chitosan tends to engulf OV2008 cells.

The inventive drug delivery system, containing paclitaxel with a fluorescence probe was studied using confocal microscopy. CTX-associated niosomes, loaded with a fluorescent-tagged paclitaxel, and chitosan delivery system were tested for in vitro drug delivery in glioma, epithelial ovarian carcinoma, and normal ovarian epithelial and astrocyte cells. The level of fluorescence of normal cells and tumor cells exposed to the fluorescently labeled paclitaxel were evaluated in in vitro by confocal microscopy. The amount of fluorescence intensity was quantified and compared due to the uptake of paclitaxel absorbed in ovarian carcinoma OV2008 and normal ovarian epithelial MCC3 cells. Preferential delivery to OV2008 was seen as higher paclitaxel take-up by OV2008. This is seen as higher intensity for OV2008 than MCC3 due to the affinity of chitosan to MUC1 over-expressed in OV2008. Incorporation of niosomes containing a fluorescently-conjugated paclitaxel compound reinforced the results, as MCC3 cells exhibited very minor fluorescence, slightly above chitosan only signals, as seen in FIGS. 29 and 30, compared to significant fluorescence with paclitaxel-treated OV2008 cells, as seen in FIGS. 31 and 32, showing the CTX-niosome-chitosan delivery system resulted in preferential uptake of paclitaxel in OV2008 cells.

Attenuated Total Reflectance-Fourier Transform Infra-Red (ATR-FTIR) spectroscopy was used to test the interaction between the CTX-niosome-chitosan delivery system. The ATR-FTIR results, seen in FIG. 33, confirm the previously observed higher chitosan accumulation on the surface of OV2008 compared to MCC3. These results confirm the mucoadhesive property of chitosan and indicating its specificity in targeting MUC1 overexpressing tumor cells. Moreover, quantification of the level of fluorescently-labeled paclitaxel in OV2008 cells, compared to MCC3 control cells, shows the combination of CTX and chitosan provide specific targeting and an increase in anti-tumor efficacy, as seen in FIG. 34.

The localized drug delivery system exhibited enhanced targeting ability through specific interactions between chitosan and MUC1 receptor overexpressed on cell surfaces of specific cancers, such as glioma, colon, breast, lung pancreatic cancers, and epithelial ovarian cancer. Similarly, the incorporation of CTX binds preferentially to tumor cells of neuroectodermal origin but not to normal cells) to further improve the specific delivery of drugs to tumor cells such as glioma.

The system demonstrates a new approach in the treatment of cancers, through the controlled and targeted delivery to tumor cells (the release time and dosage can be accurately controlled) while sparing normal cells. Specifically binds to neuroectodermal tumors, e.g., glioma, but not to normal tissues. It has been shown that there is a specific interaction between chitosan and Mucin1 (MUC1) receptors over expressed in epithelial ovarian carcinoma resulting in higher chitosan accumulation on the cancer cell surface than on normal ovarian epithelial cells. Incorporating CTX in the chitosan network enhanced the specific targeting of the drug delivery system, which already benefits from the intrinsic interaction of MUC1 with chitosan.

The niosomal-chitosan delivery system, with CTX associated with the niosomes as the targeting ligand, shows an increase in anti-tumor efficacy because of the enhanced tumor targeting and its controlled and localized delivery. This allows for enhanced control of therapy, as the release time and dosage administered to cancer cells can be accurately controlled. The use of CTX allows for enhanced cellular uptake of the chemotherapeutic In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

SEQUENCE LISTING

<110> University of South Florida
<120> Enhanced Targeted Drug Delivery System via Chitosan Hydrogel and Chlorotoxin
<130> 1372.982.PRC <150> 61/971328
<151> 2014-03-27
<160> 1
<170> PatentIn version 3.5
<210> 1
<211> 36
<212> PRT
<213> *Leiurus quinquestriatus*
<400> 1
Met Cys Met Pro Cys Phe Thr Thr Asp His Gln Met Ala Arg Lys Cys
5 10 15
Asp Asp Cys Cys Gly Gly Lys Gly Arg Gly Lys Cys Tyr Gly Pro Gln
20 25 30
Cys Leu Cys Arg
35 hexadecyl diglycerol ether; sorbitan monopalmitate, sorbitan monostearate, poly-24-oxyethylene cholesteryl ether, polysorbate 20, Span detergents, Brij detergents, polyoxyethylene, and polysorbates.

3. The drug delivery medium of claim 1, wherein the niosome further comprises at least one negative charged molecules selected from the group consisting of polyoxyethylene (61), sorbitan monostearate, cetyl sulphate, phosphatidic acid, phosphatidyl serine, oleic acid, palmitic acid, and dicetyl phosphates.

4. The drug delivery medium of claim 1, wherein the niosome further comprises at least one cholesterol.

5. The drug delivery medium of claim 4, wherein the niosome further comprises sorbitan monostearate, at least one cholesterol, and dicetyl phosphate at a ratio of 1:1:0.1.

6. The drug delivery medium of claim 1, wherein the polymer hydrogel further comprises β-glycerophosphate

```
                         SEQUENCE LISTING

<160> NUMBER OF SEQ ID NOS: 1

<210> SEQ ID NO 1
<211> LENGTH: 36
<212> TYPE: PRT
<213> ORGANISM: Leiurus quinquestriatus

<400> SEQUENCE: 1

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
        35
```

What is claimed is:

1. A drug delivery medium, comprising:

at least one niosome further comprising:

a hydrophobic bilayer defining an interior hydrophilic space, wherein the hydrophobic bilayer has an exterior surface and an interior surface;

at least one hydrophobic chemotherapeutic drug integrated into the hydrophobic bilayer, at least one hydrophilic chemotherapeutic drug encapsulated in the interior hydrophilic space, or a combination thereof;

at least one protein associated with the exterior surface of the hydrophobic bilayer of the at least one niosome, wherein the at least one protein comprises SEQ ID No. 1; and a polymer hydrogel, wherein the at least one niosome is embedded in the polymer hydrogel, where the polymer hydrogel is selected from the group consisting of chitosan, poly-NIPAAm, poly(vinyl methyl ether), poly (2-(2-methoxyethoxy)ethyl methacrylate), acryloyl-L-proline methyl ester, poly(N, N-diethylacrylamide), poly(N-vinylcaprolactam), poly-(ethylene oxide) and poly(propylene oxide) block copolymer, and poly(acrylamide).

2. The drug delivery medium of claim 1, wherein the niosome further comprises at least one surfactant selected from the group consisting of crown ether amphiphiles bearing a steroidal moiety, 1,2-dialkyl glycerol polyoxyethylene ether, hexadecyl poly-5-oxyethylene ether, hexadecyl poly-5-oxyethylene ether; octadecyl poly-5-oxyethylene ether;

polyol, glycerol, pentaerythritol, ethylene glycol, glycerin, castor oil, sucrose polyethylene glycol, polypropylene glycol, poly(tetramethylene ether) glycol, polyoses, trehalose, glycogen, cellulose, chitin, amylose, or amylopectin glycogen.

7. The drug delivery medium of claim 6, wherein the polymer hydrogel comprises chitosan and β-glycerophosphate at a ratio of 4.0:1.

8. The drug delivery medium of claim 1, further comprising a plurality of biodegradable polymer hydrogel layers, wherein the niosomes are embedded in the hydrogel layers, and wherein the adjoining layers have distinct properties.

9. A method of preparing a drug delivery medium, comprising the steps of:

forming at least one niosome, further comprising:

combining at least one surfactant, at least one cholesterol, and at least one hydrophobic drug;

adding a solvent to the at least one surfactant, and the at least one cholesterol to form a solution;

evaporating the solvent to form a thin film;

hydrating the thin film with a hydrophilic drug;

associating the at least one niosome with at least one protein wherein the at least one protein comprises SEQ ID No. 1, further comprising:

suspending the at least one protein in a solution that is isotonic to the at least one niosome;

adding the at least one niosome to the suspension of at least one protein;

permitting the at least one niosome to equilibrate with the at least one protein solution to form at least one modified noisome, wherein the at least one protein associated with the exterior surface of the hydrophobic bilayer of the at least one niosome; and embedding the at least one modified niosome in a hydrogel, wherein the hydrogel is selected from the group consisting of chitosan, poly-NIPAAm, poly(vinyl methyl ether), poly(2-(2 methoxyethoxy)ethyl methacrylate), acryloyl-L-proline methyl ester, poly(N,N-diethylacrylamide), poly(N-vinylcaprolactam) (PVCL), poly-(ethylene oxide) and poly(propylene oxide) block copolymer, and poly(acrylamide).

10. The method of claim 9, wherein the at least one surfactant is selected from the group consisting of crown ether amphiphiles bearing a steroidal moiety, 1,2-dialkyl glycerol polyoxyethylene ether, hexadecyl poly-5-oxyethylene ether, hexadecyl poly-5-oxyethylene ether; octadecyl poly-5-oxyethylene ether; hexadecyl diglycerol ether; sorbitan monopalmitate, sorbitan monostearate, poly-24-oxyethylene cholesteryl ether, polysorbate 20, Span detergents, Brij detergents, polyoxyethylene, and polysorbates.

11. The method of claim 9, wherein the niosome further comprises at least one negative charged molecule selected from the group consisting of polyoxyethylene (61), sorbitan monostearate, cetyl sulphate, phosphatidic acid, phosphatidyl serine, oleic acid, palmitic acid, and dicetyl phosphates.

12. The method of claim 9, wherein the solution is evaporated by passing $N_2$ gas over the solution.

13. The method of claim 9, further comprising extruding the resulting niosomes.

14. The method of claim 9, further comprising separating the niosomes from unincorporated hydrophilic drug by ultracentrifugation.

15. The method of claim 9, wherein the hydrogel is chitosan.

16. The method of claim 15, further comprising adding β-glycerophosphate to the chitosan solution.

17. The method of claim 16, wherein the β-glycerophosphate is added to the chitosan solution at a ratio of 4.0:1.

18. The method of claim 15, wherein the ratio of niosome to chitosan ranges from (0.15):1 to (0.45):1.

19. A method of treating a MUC1 overexpressing cancer, comprising:

contacting the MUC1 overexpressing cancer with a drug delivery system, where the drug delivery system comprises:

at least one niosome further comprising:

a hydrophobic bilayer defining an interior hydrophilic space, wherein the hydrophobic bilayer has an exterior surface and an interior surface;

at least one hydrophobic chemotherapeutic drug integrated into the hydrophobic bilayer, at least one hydrophilic chemotherapeutic drug encapsulated in the interior hydrophilic space, or a combination thereof;

at least one protein associated with the exterior surface of the hydrophobic bilayer of the at least one niosome, wherein the at least one protein comprises SEQ ID No. 1; and a polymer hydrogel, wherein the at least one niosome is embedded in the polymer hydrogel, where the polymer hydrogel is selected from the group consisting of chitosan, poly-NIPAAm, poly(vinyl methyl ether), poly(2-(2-methoxyethoxy)ethyl methacrylate), acryloyl-L-proline methyl ester, poly(N,N-diethylacrylamide), poly(N-vinylcaprolactam), poly-(ethylene oxide) and poly(propylene oxide) block copolymer, and poly(acrylamide);

wherein the MUC1 overexpressing cancer is colon cancer, breast cancer, ovarian cancer, lung cancer, or pancreatic cancer.

20. The method of claim 19, wherein the MUC1 overexpressing cancer is epithelial ovarian cancer.

21. The drug delivery medium of claim 1, wherein the at least one protein and the exterior surface of the hydrophobic bilayer of the at least one noisome are associated by hydrogen bonding.

* * * * *